(12) United States Patent
Binder et al.

(10) Patent No.: US 11,083,634 B2
(45) Date of Patent: Aug. 10, 2021

(54) METHOD AND DEVICE FOR PACKING A BODY CAVITY AND DELIVERING A MEDICAMENT TO A SUBJECT

(71) Applicant: Binyarco LLC, Bentleyville, OH (US)

(72) Inventors: Jeffrey E. Binder, Bentleyville, OH (US); Arthur L. Clements, III, Chagrin Falls, OH (US); Gregory Weisberg, Cleveland Heights, OH (US); Paul L. Erickson, Eastlake, OH (US); Stephanie A. Harrington, Hudson, OH (US)

(73) Assignee: BINYARCO LLC, Bentleyville, OH (US)

( * ) Notice: Subject to any disclaimer, the term of this patent is extended or adjusted under 35 U.S.C. 154(b) by 144 days.

(21) Appl. No.: 15/998,478

(22) Filed: Aug. 15, 2018

(65) Prior Publication Data
US 2019/0053957 A1    Feb. 21, 2019

Related U.S. Application Data

(60) Provisional application No. 62/545,850, filed on Aug. 15, 2017.

(51) Int. Cl.
*A61M 31/00* (2006.01)
*A61F 13/20* (2006.01)
(Continued)

(52) U.S. Cl.
CPC .......... *A61F 13/2005* (2013.01); *A61B 17/24* (2013.01); *A61F 13/126* (2013.01);
(Continued)

(58) Field of Classification Search
CPC .... A61F 13/2005; A61F 6/08; A61F 13/2074; A61F 13/2022; A61F 5/0093; A61F 2013/00476; A61F 6/12; A61F 13/26; A61F 13/266; A61F 13/2011; A61F 13/2034; A61F 2250/0067; A61F 13/2031; A61F 13/204; A61F 13/38; A61F 2013/4729; A61K 9/0036; A61K 9/0034; A61K 9/0012; A61K 9/0043; A61K 9/02; A61K 9/025; A61M 31/002; A61M 31/00; A61M 31/007; A61M 2210/0618; A47L 13/44; A47L 13/46; A47K 7/00–7/08
See application file for complete search history.

(56) References Cited

U.S. PATENT DOCUMENTS 467,599 A * 1/1892 Ellis et al. ............. A61M 31/00
3,818,911 A * 6/1974 Fournier ................. A61F 13/38
604/1

(Continued)

*Primary Examiner* — Emily L Schmidt
(74) *Attorney, Agent, or Firm* — Tarolli, Sundheim, Covell & Tummino LLP

(57) ABSTRACT

A medical packing device for use within a body cavity of a subject is provided. The medical packing device comprises an absorbent member having at least a first major side surface and at least one depression that is formed in the first major side surface and has a predetermined shape and volume. The at least one depression is defined by a continuous perimeter wall that is formed in the first major side surface and forms a reservoir capable of receiving and retaining a volume of a medicament therein.

33 Claims, 13 Drawing Sheets

(51) Int. Cl.
*A61F 13/12* (2006.01)
*A61B 17/24* (2006.01)
*A61B 17/00* (2006.01)
*A61B 17/12* (2006.01)

(52) U.S. Cl.
CPC ....... *A61M 31/002* (2013.01); *A61B 17/1204* (2013.01); *A61B 17/12104* (2013.01); *A61B 2017/00893* (2013.01); *A61B 2017/00898* (2013.01); *A61B 2017/12004* (2013.01); *A61F 13/2028* (2013.01)

(56) References Cited

U.S. PATENT DOCUMENTS

| | | | |
|---|---|---|---|
| 3,831,605 A * | 8/1974 | Fournier | A61F 13/263 604/17 |
| 5,387,206 A | 2/1995 | Valentine et al. | |
| 5,584,822 A | 12/1996 | Lively et al. | |
| 6,517,509 B1 | 2/2003 | Shippert | |
| 7,294,138 B2 | 11/2007 | Shippert | |
| 2010/0114000 A1 * | 5/2010 | Park | A47K 7/03 604/2 |
| 2010/0324467 A1 * | 12/2010 | Hasse | A61F 13/26 604/11 |
| 2012/0010587 A1 * | 1/2012 | Smet | A61F 13/2051 604/379 |
| 2012/0053544 A1 * | 3/2012 | Drevik | A61F 13/26 604/359 |
| 2016/0235953 A1 | 8/2016 | Hsu | |

\* cited by examiner

US 11,083,634 B2

METHOD AND DEVICE FOR PACKING A BODY CAVITY AND DELIVERING A MEDICAMENT TO A SUBJECT

RELATED APPLICATION

This application claims priority from U.S. Provisional Application No. 62/545,850, filed 15 Aug. 2017, the subject matter of which is incorporated herein by reference in its entirety.

TECHNICAL FIELD

This disclosure relates to devices and methods for delivery of drugs and pharmaceutical compositions. This disclosure also relates to a device for treating epistaxis, that is, a device for treating nosebleeds, and a method for making and using same. The device can also be used for intranasal drug delivery or drug delivery at other anatomical locations.

BACKGROUND

Nosebleed, scientifically called epistaxis, is a common problem worldwide. Blunt trauma to the nose, sneezing, inhaling dry air and certain other factors can cause nosebleed in a subject. Several mechanical devices have been described to treat epistaxis. These devices largely rely on applying pressure to the inside of the nose through various devices such as intranasal balloon insufflation, clamping instruments or soft intranasal sponges that are placed alongside the site of bleeding to apply mechanical pressure. There is a need for an improved device for insertion into the nasal passage for treating epistaxis. There is also a need for a device for delivering drugs intranasally.

SUMMARY

In an aspect, a medical packing device for use within a body cavity of a subject is provided. The medical packing device comprises an absorbent member having at least a first major side surface and at least one depression that is formed in the first major side surface and has a predetermined shape and volume. The at least one depression is defined by a continuous perimeter wall that is formed in the first major side surface and forms a reservoir capable of receiving and retaining a volume of a medicament therein.

In an aspect, a medical packing device for use within a body cavity of a subject is provided. The medical packing device comprises an absorbent member having at least a first major side surface and at least one depression that is formed in the first major side surface and has a predetermined shape and volume. The at least one depression is defined by a continuous perimeter wall that is formed in the first major side surface and forms a reservoir capable of receiving and retaining a volume of a medicament therein. A handle is connected to a proximal end of the absorbent member.

In an aspect, a method for delivering a medicament to a subject is provided. A medical packing device is provided. The medical packing device comprises an absorbent member having at least a first major side surface and at least one depression that is formed in the first major side surface and has a predetermined shape and volume. The at least one depression is defined by a continuous perimeter wall that is formed in the first major side surface and forms a reservoir capable of receiving and retaining a volume of a medicament therein. At least a portion of the absorbent member is inserted into a body cavity of the subject for a time sufficient to allow delivery of the medicament from the at least one depression to anatomical tissue adjacent to the at least one depression in the body cavity.

In an aspect, a medical packing device for use within a body cavity of a subject is provided. The medical packing device comprises an absorbent member having oppositely disposed proximal and distal ends and an aperture extending through the absorbent member at the proximal end. A handle has a pinhole that is aligned with the aperture. A pin laterally extends through each of the pinhole and the aperture to secure the absorbent member to the handle. The absorbent member being pivotable with respect to the handle about the pin.

In an aspect, a medical packing device for use within a body cavity of a subject is provided. An absorbent member has oppositely disposed proximal and distal ends. A handle has oppositely disposed proximal and distal ends. The handle has a receiving portion with a distal portion disposed towards the distal end of the handle and a proximal portion that is adjacent and proximal to the distal portion. The distal portion of the receiving portion has a distal portion surface with a convex-shaped portion. The receiving portion has a receiving hollow that extends from a receiving opening in the distal portion surface into the proximal portion. The receiving portion has first and second major side surfaces for gripping the receiving portion of the handle. The proximal end of the absorbent member is connected to the handle and seated within the receiving hollow.

BRIEF DESCRIPTION OF THE DRAWINGS

For a better understanding, reference may be made to the accompanying drawings, in which.

DESCRIPTION OF EMBODIMENTS

Figure 1:
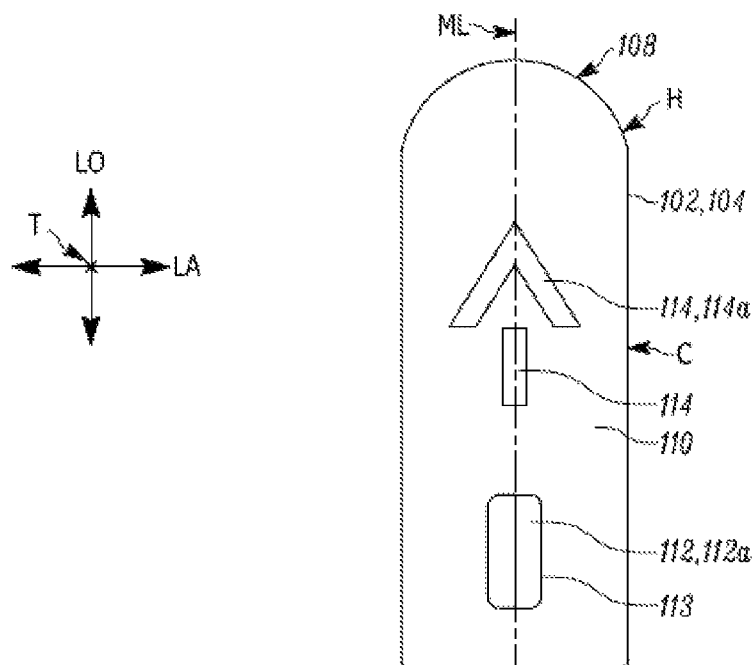
FIG. 1 is a front side view of an element of a medical packing device according to one aspect of the present invention, in a first configuration.
Figure 2:
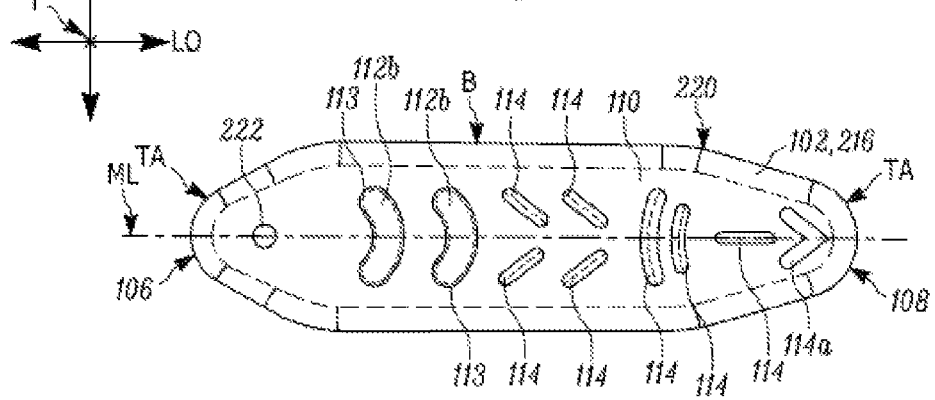
FIG. 2 is a front side view of an element of the aspect of FIG. 1, in a second configuration.
Figure 3:
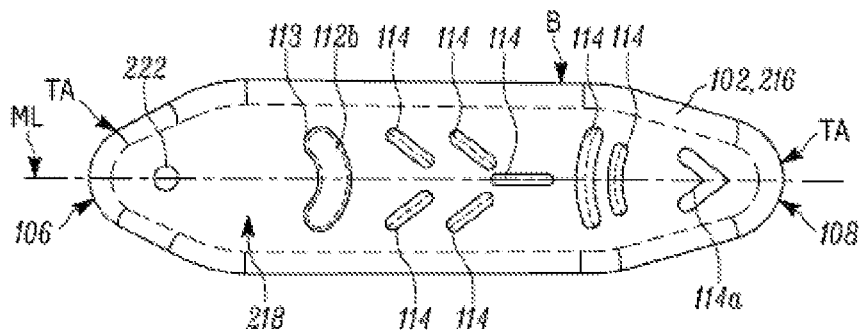
FIG. 3 is a rear side view of the element of the aspect of FIG. 2.

Unless defined otherwise, all technical and scientific terms used herein have the same meaning as is commonly understood by one of ordinary skill in the art to which the present disclosure pertains.

As used herein, the term "subject" can refer to any warm-blooded organism including, but not limited to, human beings, pigs, rats, mice, dogs, goats, sheep, horses, monkeys, apes, rabbits, cattle, farm animals, livestock, etc.

As used herein, the term "user" can be used interchangeably to refer to an individual who prepares for, assists with, and/or performs a procedure.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, the phrase "at least one of X and Y" can be interpreted to include X, Y, or a combination of X and Y. For example, if an element is described as having at least one of X and Y, the element may, at a particular time, include X, Y, or a combination of X and Y, the selection of which could vary from time to time. In contrast, the phrase "at least one of X" can be interpreted to include one or more Xs.

It will be understood that when an element is referred to as being "on," "attached" to, "connected" to, "contacting," etc., another element, it can be directly on, attached to, connected to or contacting the other element or intervening elements may also be present. It will also be appreciated by those of skill in the art that references to a structure or feature that is disposed "adjacent" another feature may not have portions that overlap or underlie the adjacent feature.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or Figures unless specifically indicated otherwise.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual and partial numbers within that range, for example, 1, 2, 3, 4, 5, 5.5 and 6. This applies regardless of the breadth of the range.

The invention comprises, consists of, or consists essentially of the following features, in any combination.

FIG. 1 depicts a medical packing device 100 comprising an absorbent member 102. The medical packing device 100 is for use within a body cavity of a subject such as a naturally present anatomic cavity (e.g., a nasal cavity) or a cavity that is not naturally present (e.g., a cavity created surgically or created as a result of trauma). As shown in FIG. 1, the absorbent member 102 can have a finger-shaped configuration. It will be appreciated that the absorbent member 102 of the medical packing device 100 may have various alternate configurations, some of which will be discussed below. FIGS. 1-23 depict exemplary alternate configurations of the absorbent member 102. Although FIGS. 1-23 depict example alternate configurations of the absorbent member 102, any of these configurations may, or may not, include features, and accordingly the function of those features, of any other of the configurations whether expressly stated, shown, or not. Further, common elements shared between the alternate configurations of the absorbent member 102 include common reference characters.

FIG. 1. depicts an example alternate configuration for the absorbent member 102, referred to as an absorbent member A 104. The absorbent member A 104 has oppositely disposed and longitudinally spaced proximal and distal ends 106, 108 and at least a first major side surface 110. The term "longitudinal" is used herein to indicate a substantially vertical direction, in the orientation of FIG. 1, and is shown at LO in FIG. 1. The first major side surface 110 may be an outward facing surface of any three-dimensionally shaped absorbent member 102, such as, but not limited to, any outward facing surface of a rectangular-shaped absorbent member, a cylindrical-shaped absorbent member, a spherical-shaped absorbent member, a cone-shaped absorbent member, a triangular prism-shaped absorbent member. The absorbent member A 104 is shown in FIG. 1 as having a substantially finger-shaped configuration in the form of a cylindrical-shaped portion (shown at C in FIG. 1) and a hemispherical-shaped distal end 108 (shown at H in FIG. 1). Although the absorbent member A 104 is shown having a hemispherical-shaped distal end 108, the proximal end 106 and/or the proximal and distal ends 106, 108 may have the hemispherical-shaped configuration H.

The absorbent member A 104 may include at least one depression 112 that is formed in at least the first major side surface 110 and has a predetermined shape and volume, and thus the at least one depression 112 does not include the micro-structure of a material used to form the absorbent member A 104, such as, but not limited to, the naturally-occurring pores of such a material. The at least one depression 112 is defined by a continuous perimeter wall 113 that is formed in the first major side surface 110 and forms a reservoir capable of receiving and retaining a volume of a medicament therein. For example, the at least one depression 112 may be a blind hole, a bowl, a pocket, a dimple, or any other similar structure that extends into the absorbent member 102 from the first major side surface 110 without penetrating through the absorbent member 102. The at least one depression 112 is not a channel extending along the first major side surface 110, or any other major side surface, of the absorbent member 102 or a fenestration/aperture penetrating through the absorbent member 102. In one example, the at least one depression 112 of the absorbent member A 104 may be rectangular-shaped (shown here as rectangular-shaped depression 112a), however, other shapes are possible. The depression 112 may be located at any desired position along the absorbent member A 104 in order to be positioned adjacent to a predetermined location in a subject's cavity, such as a subject's nasal cavity, when the medical packing device 100 is inserted into the subject's cavity.

At least the first major side surface 110 of the absorbent member A 104 may also include at least one impressed marking 114. In particular, the first major side surface of the absorbent member A 104 is shown in FIG. 1 as having a plurality of impressed markings 114. The absorbent member A 104 may be rigid and have a low degree of flexibility. Thus, each of the impressed markings 114 form weaknesses or creases in the absorbent member A 104 so that the absorbent member A 104 is at least partially capable of bending along the impressed markings 114 in order to avoid and/or bend around obstructions in a subject's cavity, such as a subject's nasal cavity, during insertion of the device 100. In other words, each of the impressed markings 114 at least partially acts as a flex locus so that the absorbent member A 104 is at least partially bendable along each of the impressed markings 114.

At least a portion of the impressed markings 114 may serve additional functions. For example, at least one of the impressed markings 114 on at least the first major side surface 110 of the absorbent member A 104 may point toward the distal end 108 of the absorbent member A 104. The distal end 108 of the absorbent member A 104 may be the portion of the absorbent member A 104 that is inserted first into the nasal cavity of a subject. Thus, the at least one impressed marking 114 that points toward the distal end of the absorbent member A 104 at least partially acts as a directional marking (shown here as impressed directional marking 114a). Additionally, each of the impressed markings 114 may be longitudinally spaced apart from at least one other of the impressed markings 114 at a predetermined distance so that the longitudinally spaced markings 114 form graduation marks on the absorbent member A 104. The impressed markings 114 forming graduation markings may be used, for example, to measure how far from a predetermined point on the device 100 (such as the distal end 108 of the absorbent member A 104 and/or the proximal end 106 of the absorbent member A 104) blood has progressed or flowed, measure how far the absorbent member A 104 has been inserted into the nasal cavity, and measure where an epistaxis is located is located in the nasal cavity. Each of the impressed markings 114 present on the absorbent member A 104 may be perpendicular to a longitudinal axis ML of the absorbent member A 104, at an acute angle with respect to the longitudinal axis ML of the absorbent member A 104, at an obtuse angle with respect to the longitudinal axis ML of the absorbent member A 104, spaced from the longitudinal axis ML of the absorbent member A 104, overlap the longitudinal axis ML of the absorbent member A 104, arcuate, rectangular, circular, ovoid, triangular, pointed, in any other configuration, or any combination thereof.

FIGS. 2-5 depict an example alternate configuration for the absorbent member 102, referred to as an absorbent member B 216. The absorbent member B 216 may have oppositely disposed first and second major side surfaces 110, 218, an edge 220 transversely extending between the first and second major side surfaces 110, 218, and a blade-shaped configuration (shown at B in FIGS. 2-3). The term "transverse" is used herein to indicate a direction that extends perpendicular to both the "longitudinal" direction and the plane of the page, in the orientation of FIG. 2, and is shown at T in FIG. 2. At least one of the proximal and distal ends 106, 108 of the absorbent member B 216 may have a tapered configuration (shown at TA in FIGS. 2-3). The absorbent member B 216 may have an aperture 222 located at the proximal end 106 of the absorbent B 216 and transversely extending between the first and second major side surfaces 110, 218. The absorbent member B 216 may be attached to a handle 2644 through the aperture 222 in the manner as described below. Alternatively, the absorbent member B 216 may be used without the handle 2644. In such case, a string (not shown) may be tied through the aperture 222 so that the absorbent member B 216 can be at least partially manipulated by a user through the string.

The absorbent member B 216 includes the at least one depression 112 on each of the first and second major side surfaces 110, 218. The at least one depression 112 on the first major side surface 110 is defined by the continuous perimeter wall 113 that is formed in the first major side surface 110 and the at least one depression 112 on the second major side surface 218 is defined by a continuous perimeter wall 113 that is formed in the second major side surface 218. As shown in FIGS. 2-5, the absorbent member B 216 includes a plurality of depressions 112 on the first major side surface 110, and at least one depression 112 on the second major side surface 218. The depressions 112 of the absorbent member B 216 may be arcuate-shaped (shown here as arcuate-shaped depression 112b). The absorbent member B 216 may include the at least one impressed marking 114 on at least one of the first and second major side surfaces 110, 218. In particular, the absorbent member B 216 is shown in FIGS. 2-5 as having a plurality of impressed markings 114 located on the first and second major side surfaces 110, 218 of the absorbent member B 216.

Figure 4:
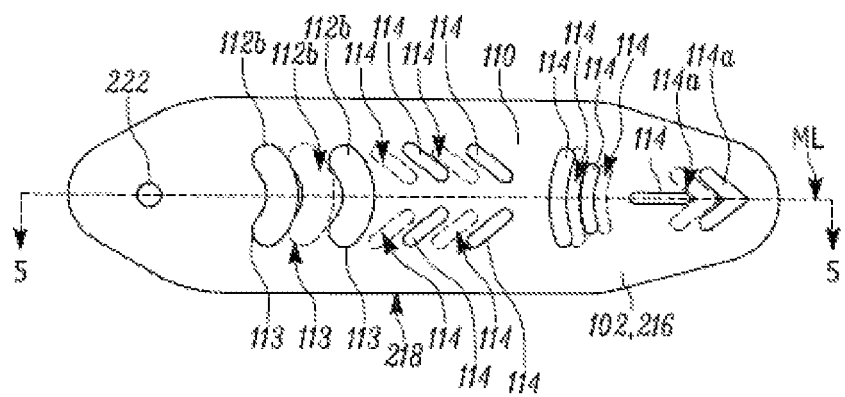
FIG. 4 is a schematic front side view of the element of the aspect of FIG. 2.
Figure 5:
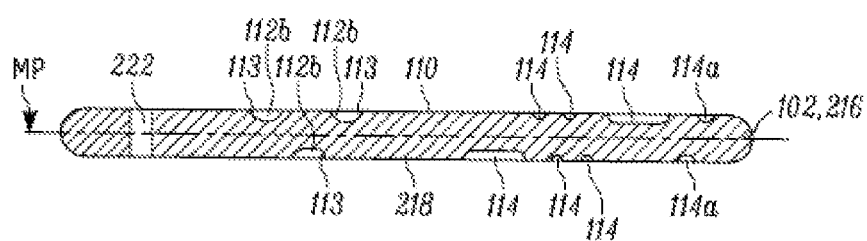
FIG. 5 is a cross-sectional view taken along line 5-5 in FIG. 4.
Figure 6:
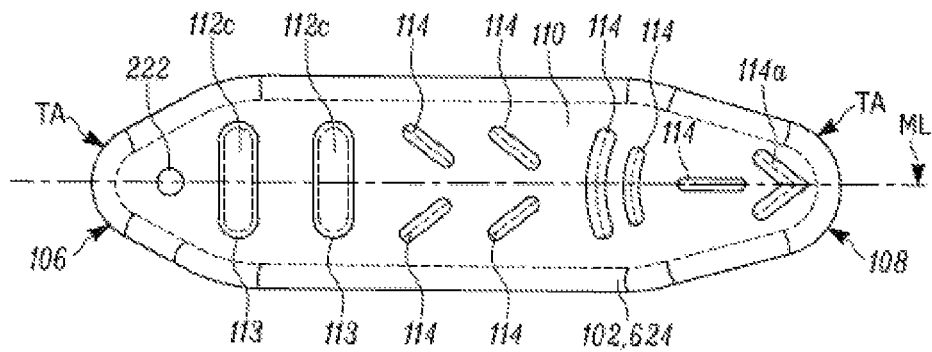
FIG. 6 is a front side view of an element of the aspect of FIG. 1, in a third configuration.
Figure 7:
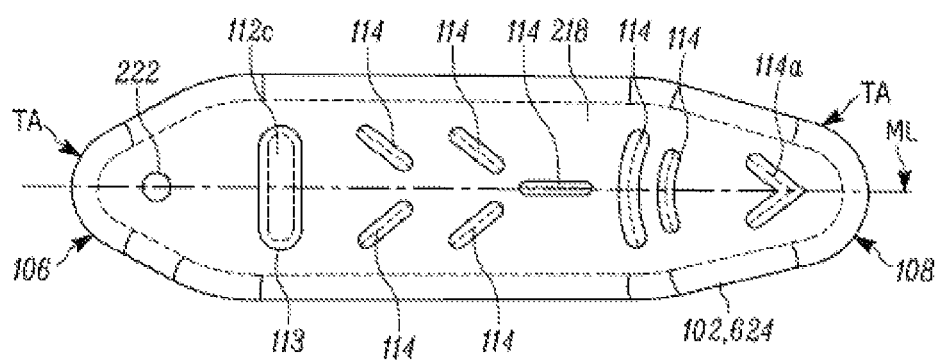
FIG. 7 is a rear side view of the element of the aspect of FIG. 6.
Figure 8:
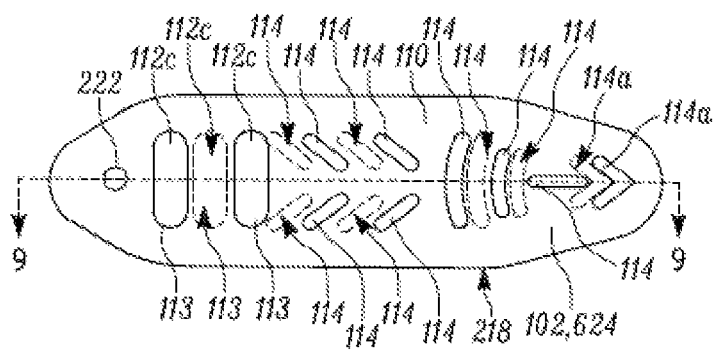
FIG. 8 is a schematic front side view of the element of the aspect of FIG. 6.
Figure 9:
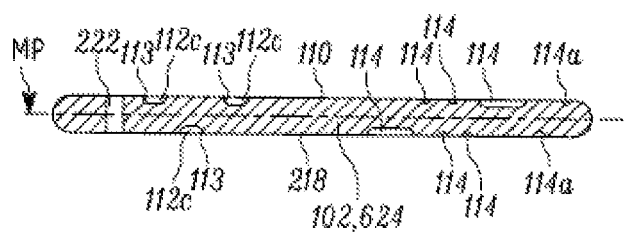
FIG. 9 is a cross-sectional view taken along line 9-9 in FIG. 8.

As shown in FIGS. 4-5, the at least one depression 112 on the first major side surface 110 is longitudinally staggered (i.e., staggered about a mid-plane MP of the absorbent member B 216) with respect to a second depression 112 on the second major side surface 218 of the absorbent member B 216 and the at least one impressed marking 114 on the first major side surface 110 is longitudinally staggered with respect to a second impressed marking 114 on the second major side surface 218 of the absorbent member B 216. In particular, the plurality of depressions 112 on the first major side surface 110 are longitudinally staggered with respect to the at least one depression 112 on the second major side surface 218. Further, the plurality of impressed markings 114 on the first major side surfaces 110 are longitudinally staggered with respect to the impressed markings 114 on the second major side surface 218. The longitudinal staggering of the depressions 112 and/or the impressed markings 114 may be at least partially helpful in avoiding over-compressed longitudinal portions of the absorbent member B 216. An over-compressed section of the absorbent member B 216 may take more time to hydrate, soften and expand than what may be desirable. Thus, by staggering the depressions 112 and the impressed markings 114, these over-compressed longitudinal portions of the absorbent member B 216 are avoided.

FIGS. 6-9 depict an example alternate configuration for the absorbent member 102, referred to as an absorbent member C 624. The absorbent member C 624 is substantially similar to the absorbent member B 216, except that the absorbent member C 624 has ovoid-shaped depressions 112 (shown here as ovoid-shaped depression 112c) instead of the arcuate-shaped depressions 112b of the absorbent member B 216.

Figure 10:
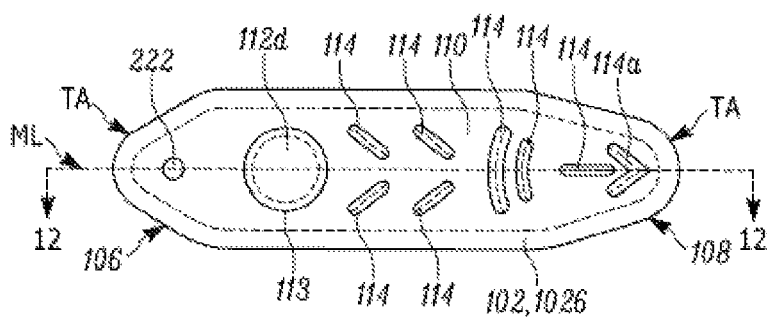
FIG. 10 is a front side view of the element of the aspect of FIG. 1, in a fourth configuration.
Figure 11:
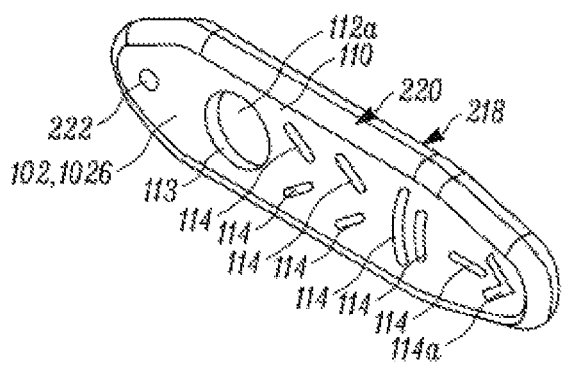
FIG. 11 is a perspective front side view of the element of the aspect of FIG. 10.
Figure 12:
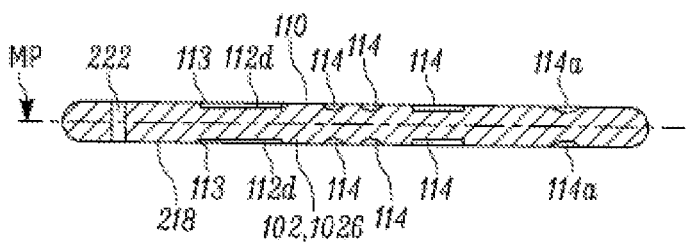
FIG. 12 is a cross-sectional view taken along line 12-12 in FIG. 10.

FIGS. 10-12 depict an example alternate configuration for the absorbent member 102, referred to as an absorbent member D 1026. The absorbent member D 1026 has the at least one depression 112 on each of the first and second major side surfaces 110, 218. In particular, the absorbent member D 1026 has a depression 112 on the first major side surface 110 and a depression 112 on the second major side surface 218. The depressions 112 of the absorbent member D 1026 are circular-shaped (shown here as circular-shaped depression 112d). As shown in FIG. 12, the at least one depression 112d on the first major side surface 110 of absorbent member D 1026 is longitudinally symmetrical (i.e., symmetrical about the mid-plane MP of the absorbent member D 1026) with a second depression 112d on the second major side surface 218 and at least one of the markings 114 on the first major side surface 110 is longitudinally symmetrical with a corresponding second marking 114 on the second major side surface 218 of the absorbent member D 1026. In particular, the depression 112d on the first major side surface 110 is longitudinally symmetrical with respect to the at least one depression 112d on the second major side surface 218. Further, the plurality of impressed markings 114 on the first major side surfaces 110 are longitudinally symmetrical with respect to the impressed markings 114 on the second major side surface 218.

Figure 13:
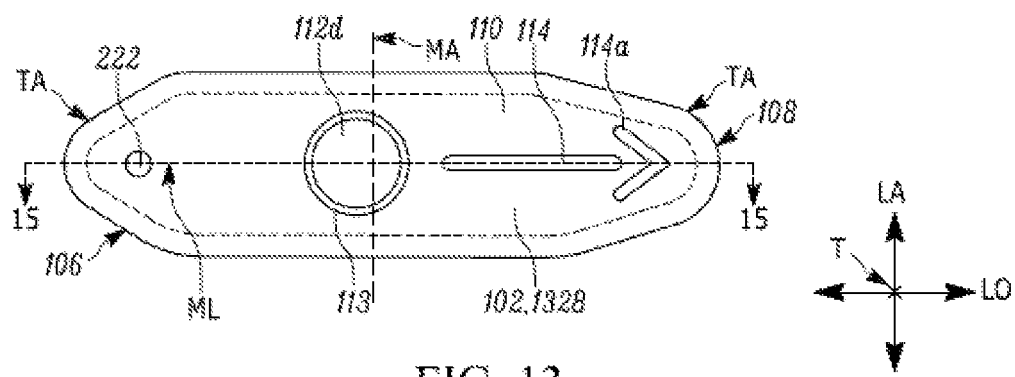
FIG. 13 is a front side view of the element of the aspect of FIG. 1, in a fifth configuration.
Figure 14:
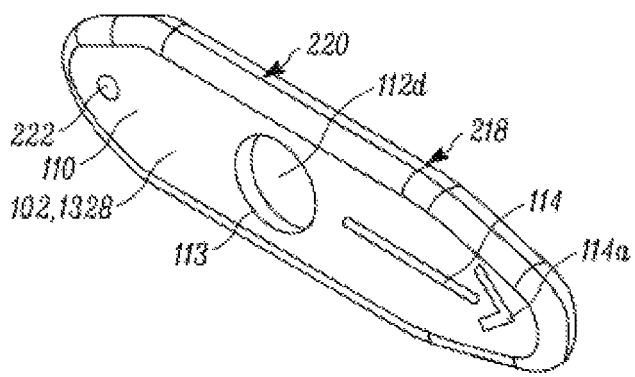
FIG. 14 is a perspective front side view of the element of the aspect of FIG. 13.
Figure 15:
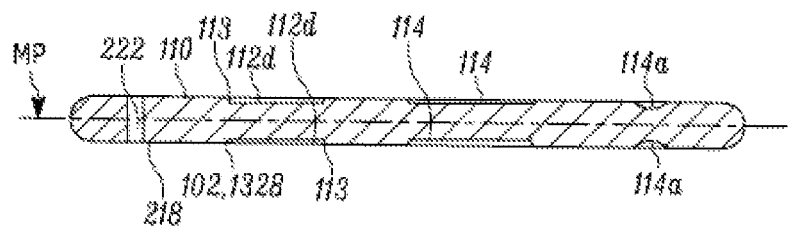
FIG. 15 is a cross-sectional view taken along line 15-15 in FIG. 13.

FIGS. 13-15 depict an example alternate configuration for the absorbent member 102, referred to as an absorbent member E 1328. The absorbent member E 1328 is substantially similar to the absorbent member D 1026, except that the depressions 112d of the absorbent member E 1328 are longitudinally spaced closer to a lateral axis MA of the absorbent member E 1328 than they are in the absorbent member D 1026. In other words, the depressions 112d of the absorbent member E 1328 are spaced farther from the proximal end 106 then the depressions 112d of the absorbent member D 1026, and the depressions 112d of the absorbent member D 1026 are farther from to the distal end 108 than the depression 112d of the absorbent member E 1328. The term "lateral" is used herein to indicate a direction substantially perpendicular to the "longitudinal" direction, and is shown as the vertical direction in the orientation of FIG. 13, and is shown at LA in FIG. 13.

Figure 16:
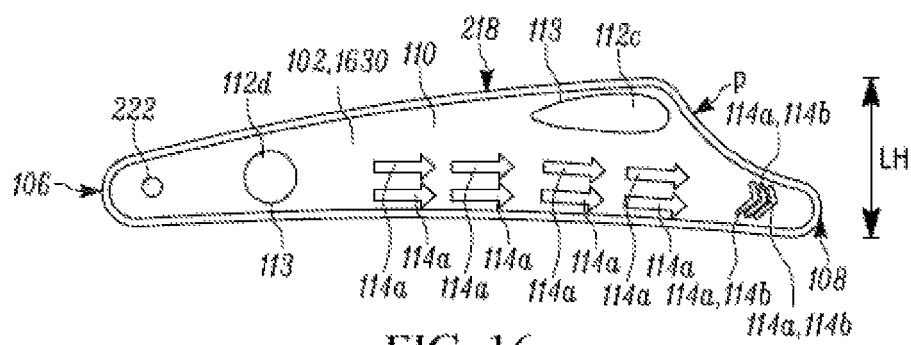
FIG. 16 is a front side view the element of the aspect of FIG. 1, in a sixth configuration.

FIG. 16 depicts an example alternate configuration for the absorbent member 102, referred to as an absorbent member F 1630. At least one of the first and second major side surfaces 110, 218 of the absorbent member F 1630 includes at least one depression 112. As shown in FIG. 16, the absorbent member F 1630 has both a circular-shaped depression 112d adjacent toward the proximal end 106 of the absorbent member F 1630 and an ovoid-shaped depression 112c adjacent toward a distal end 108 of the absorbent member F 1630. These longitudinal positions on the absorbent member F 1630 may correspond to positions in the nasal cavity that are common sites for epistaxis. Thus, having the depressions 112 being longitudinally positioned at both the proximal and distal ends 106, 108 of the absorbent member F 1630 allow the user to apply a medicament from the depressions 112 to differing common epistaxis sites in the nasal cavity.

At least one of the first and second major side surfaces 110, 218 of the absorbent member F 1630 includes at least one impressed marking 114. FIG. 16 depicts the first major side surface 110 of the absorbent member F 1630 having a plurality of impressed markings 114. At least a portion of the impressed markings 114 point towards the distal end 108 of the absorbent member F 1630, and thus act as directional markings 114a. Additionally, each of the impressed markings 114 are longitudinally spaced apart from at least one other of the impressed markings 114 at a predetermined distance so that the longitudinally spaced markings 114 form graduation marks on the absorbent member F 1630. At least a portion of the impressed markings 114 of the absorbent member F 1630 are in the form of a chevron pattern (shown here as chevron patterned impressed markings 114b).

As shown in FIG. 16, a lateral width LW of the absorbent member F 1630 diminishes at the distal end 108 of the absorbent member F 1630 in a direction opposite to the proximal end 106 of the absorbent member F 1630. In particular, the distal end 108 of the absorbent member F 1630 has a porpoise nose configuration (shown at P in FIG. 16). The porpoise nose configuration P of the absorbent member F 1630 provides the distal end 108 of the absorbent member F 1630 with the ability to more easily track through a far end of the nasal passage due to the diminished lateral width LW of the distal end 108 of the absorbent member F 1630 with respect to the remainder of the absorbent member F 1630. Although the distal end 108 of the absorbent member F 1630 is shown and described as having a porpoise nose configuration P, the lateral width LW of the absorbent member F 1630 may diminish at any portion of the absorbent member F 1630, such as at the proximal and/or distal ends 106, 108 of the absorbent member F 1630, due to a tapered configuration TA, a concaved configuration, or any other appropriate configuration.

Figure 17:
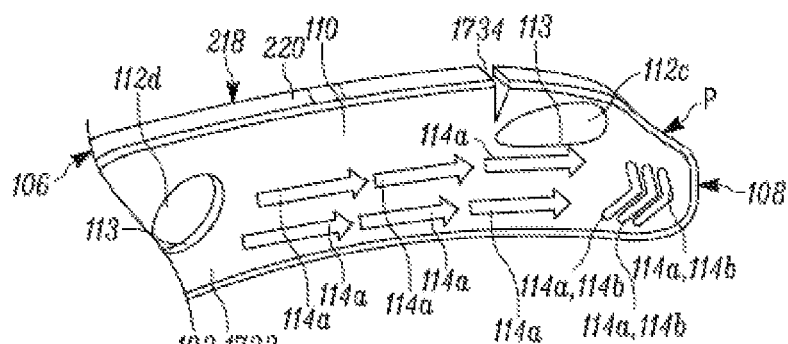
FIG. 17 is a front side view the element of the aspect of FIG. 1, in a seventh configuration.

FIG. 17 depicts an example alternate configuration for the absorbent member 102, referred to as an absorbent member G 1732. The absorbent member G 1732 is substantially similar to the absorbent member F 1630, except that the absorbent member G 1732 includes a notch 1734 that at least partially laterally extends inward from the edge 220 of the absorbent member G 1732 between the first and second major side surfaces 110, 218. The notch 1734 at least partially longitudinally separates the proximal and distal ends 106, 108 of the absorbent member G 1732 and at least partially prevents and/or impedes the flow of blood and/or bodily fluids between the proximal and distal ends 106, 108 of the absorbent member G 1732. For example, if there is an epistaxis site in the nose cavity that is adjacent to the distal end 108 of the absorbent member G 1732, the notch 1734 will at least partially prevent, impede, and/or slow the flow of blood from the distal end 108 of the absorbent member G 1732 to the proximal end 106 of the absorbent member G 1732 so that only the distal end 108 of the absorbent member G 1732 will become saturated in blood. If there is an epistaxis site in the nose cavity that is adjacent to the proximal end 106 of the absorbent member G 1732, the notch 1734 will act vice versa. This provides the user with the ability to more easily determine where in the nose cavity the epistaxis is located since at one of the proximal and distal ends 106, 108 will tend to be more saturated than the other due to the notch 1734 at least partially preventing, impeding, and/or slowing the flow of blood between the proximal and distal ends 106, 108 of the absorbent member G 1732.

Figure 18:
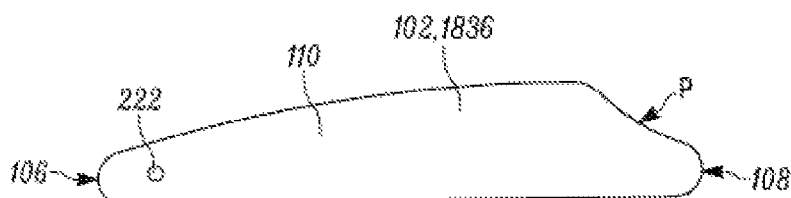
FIG. 18 is a front side view the element of the aspect of FIG. 1, in an eighth configuration.

FIG. 18 depicts an example alternate configuration for the absorbent member 102, referred to as an absorbent member H 1836. The absorbent member H 1836 is substantially similar to the absorbent member F 1630, except that the absorbent member H 1836 is free from any depressions 112 and/or impressed markings 114.

Figure 19:
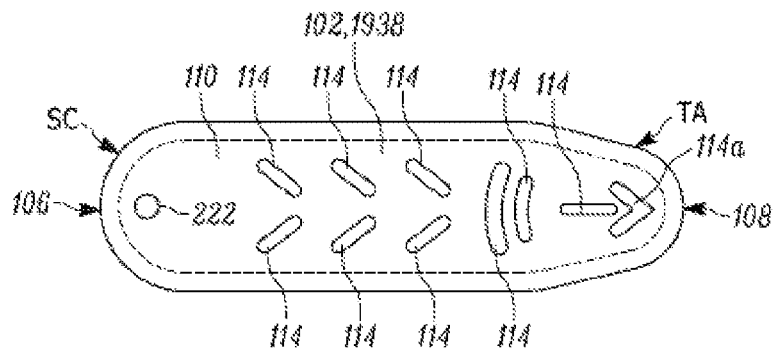
FIG. 19 is a front side view the element of the aspect of FIG. 1, in an ninth configuration.
Figure 20:
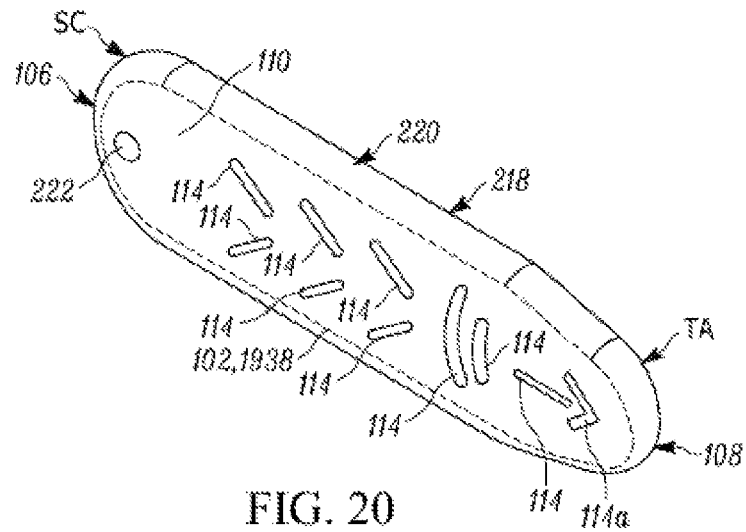
FIG. 20 is a perspective front side view of the element of the aspect of FIG. 19.

FIGS. 19-20 depict an example alternate configuration for the absorbent member 102, referred to as an absorbent member I 1938. The absorbent member I 1938 is substantially similar to the absorbent member B 216, except that the absorbent member I 1938 is free from depressions 112 and the proximal end 106 of the absorbent member I 1938 has a semi-circular shaped configuration (shown at SC in FIGS. 19-20) while the distal end 108 of the absorbent member I 1938 has the tapered configuration TA. Alternatively, both of the proximal and distal ends 106, 108 of the absorbent member I 1938 may have the semi-circular shaped configuration SC.

Figure 21:
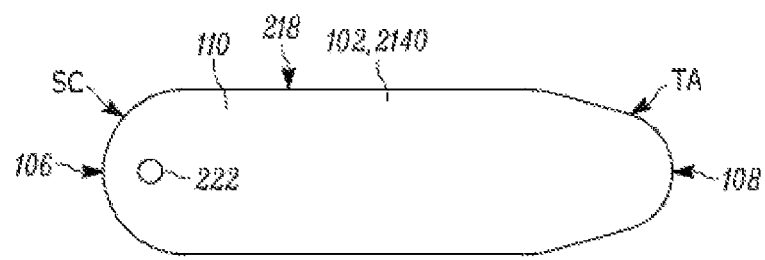
FIG. 21 is a front side view the element of the aspect of FIG. 1, in a tenth configuration.
Figure 22:
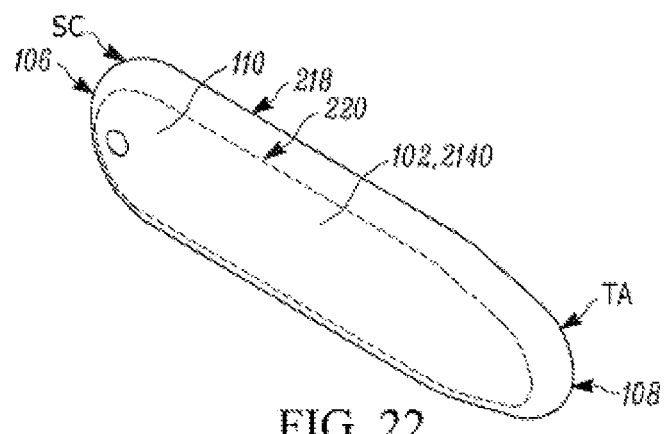
FIG. 22 is a perspective front side view of the element of the aspect of FIG. 21.

FIGS. 21-22 depict an example alternate configuration for the absorbent member 102, referred to as an absorbent member J 2140. The absorbent member J 2140 is substantially similar to the absorbent member I 1938, except that the absorbent member J 2140 is free from depressions 112 and/or impressed markings 114.

Figure 23:
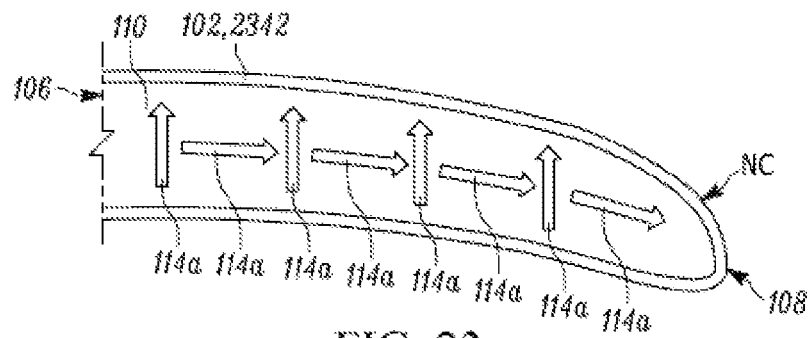
FIG. 23 is a front side view an element of the aspect of FIG. 1, in an eleventh configuration.

FIG. 23 depicts an example configuration for the absorbent member 102, referred to as an absorbent member K 2342. The absorbent member K 2342 is substantially similar to the absorbent member B 216, except that the absorbent member K 2342 is free from depressions 112 and the distal end 108 of the absorbent member K 2342 has a nose-cone shaped configuration (shown at NC in FIG. 23). A portion of the plurality of impressed markings 114 of the absorbent member K 2342 point toward the distal end 108 of the absorbent member K 2342, and another portion of the plurality of impressed markings 114 of the absorbent member K 2342 point to a predetermined portion of the edge 220 that should be positioned laterally upward when inserting the absorbent member K 2342 into the nasal cavity of a subject. Thus, the plurality of impressed markings 114 of the absorbent member K 2342 acts as directional markings 114a. Additionally, each of the impressed markings 114 may be longitudinally spaced apart from at least one other of the impressed markings 114 at a predetermined distance so that the longitudinally spaced markings 114 form graduation marks on the absorbent member K 2342.

Figure 24:
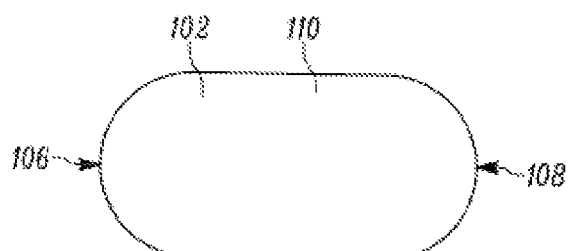
FIG. 24 is a front side view of the element of the aspect of FIG. 1, in an example use configuration.
Figure 25:
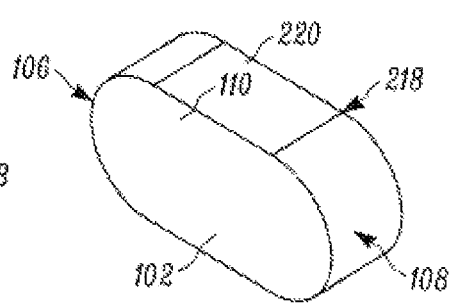
FIG. 25 is a perspective front side view of the aspect of FIG. 24.

Regardless of the configuration of the absorbent member 102, because the absorbent member 102 is absorbent, the absorbent member 102 may be moved from a compressed condition (FIGS. 1-23), to an expanded condition, such as the expanded condition of a absorbent member 102 shown in FIGS. 24-25, as the absorbent member 102 absorbs fluids, such as a subject's blood and/or bodily fluids. Although the absorbent member 102 has been shown as having the substantially cylindrical-shaped portion C and a hemispherical-shaped distal end H, or the blade-shaped configuration B, the absorbent member 102 may have any desired shape configured to fit within a cavity of a subject, such as a subject's nasal cavity. For example, the absorbent member 102 may have the blade-shaped configuration B and be about 1-4, about 1.75-3.5, about 2-2.5, or about 2.2, inches in the longitudinal direction, about 0.3-0.8, about 0.4-0.6, or about 0.5, inches in the lateral direction, and about 2-4, preferably about 2.5-3, millimeters in the transverse direction.

Figure 26:
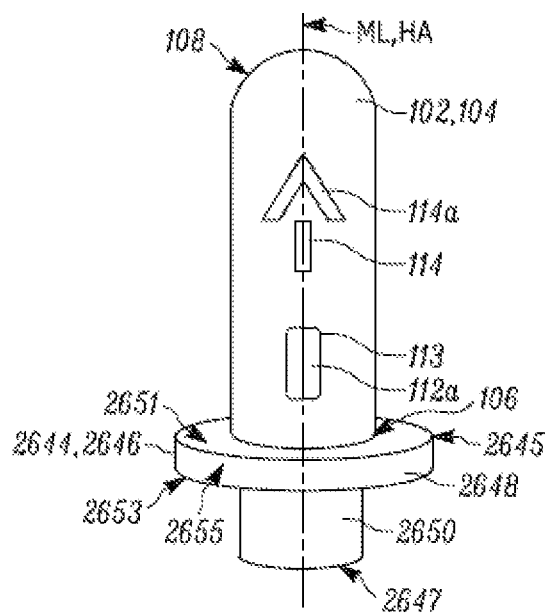
FIG. 26 is a front side view of the medical packing device according to one aspect of the present invention, in an example use configuration, and with an element in a first configuration.

As shown in FIG. 26, the medical packing device 100 may comprise a handle 2644 that is connected to the proximal end 106 of the absorbent member 102 at a receiving portion 2648 of the handle 2644. The handle has oppositely disposed distal and proximal ends 2645, 2647. The handle 2644 has a central axis HA extending therethrough. The handle 2644 may be at least one of removably or permanently connected to the proximal end 106 of the absorbent member 102. The absorbent member 102 may be at least one of removably or permanently connected to the handle 2644 by at least one connection means. The at least one connection means may be selected from a group consisting of press fit, snap fit, adhesive bonding, heat bonding, overmolding, pinning, any other appropriate connection means, and a combination thereof. The absorbent member 102 may be pivotable at an angle relative to the central axis HA of the handle 2644 so that the medical packing device 100 may be adaptable to patients having cavities, such as nasal cavities, with differing angles. The medical packing device 100 may include a selectively actuatable locking member (not shown) so that a user may be able to set, such as by pivoting, the absorbent member 102 at a predetermined angle with respect to the central axis HA of the handle 2644 such that any additional pivoting of the absorbent member 102 is selectively prevented by the locking member. Alternatively, the absorbent member 102 may be pivotally static with respect to the handle 2644.

It will be appreciated that the handle 2644 of the medical packing device 100 may have alternate configurations, some of which will be discussed below. FIGS. 26-56 depict exemplary alternate configurations of the handle 2644. Although the FIGS. 26-56, depict example alternate configurations of the handle 2644, any of these configurations may, or may not, include features, and accordingly the function of those features, of any other of the configurations whether expressly stated and shown, or not. Further, common elements shared between the alternate configurations of the handle 2644 include common reference characters.

FIG. 26 depicts an example alternate configuration for the handle 2644, referred to as a handle A 2646. The handle A 2646 has a receiving portion 2648 for removably or permanently receiving the absorbent member 102 and a gripping portion 2650 for maneuvering the medical packing device 100. The receiving portion 2648 has a distal portion 2651 disposed towards the distal end 2647 of the handle A 2646 and a proximal portion 2653 that is adjacent and proximal to the distal portion 2651. The distal portion 2651 has a distal portion surface 2655. The absorbent member A 104 and the handle A 2646 are depicted as being pivotally static with respect to one another in FIG. 26.

Figure 27:
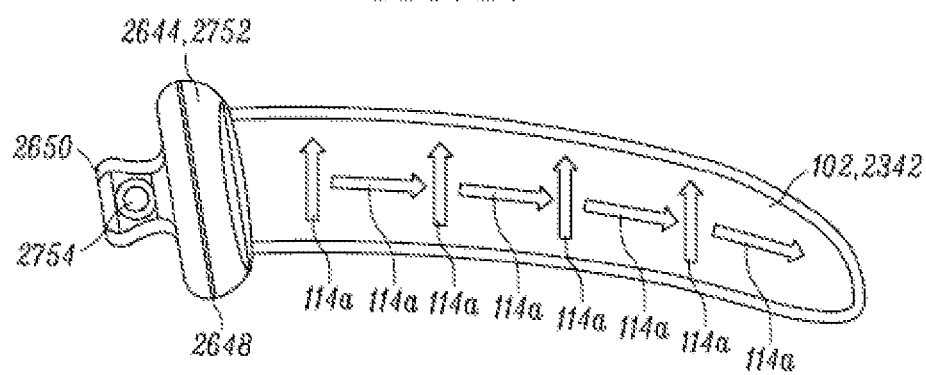
FIGS. 27-28 are front side views of the aspect of FIG. 26 in example use configurations, and with an element in a second configuration.
Figure 28:
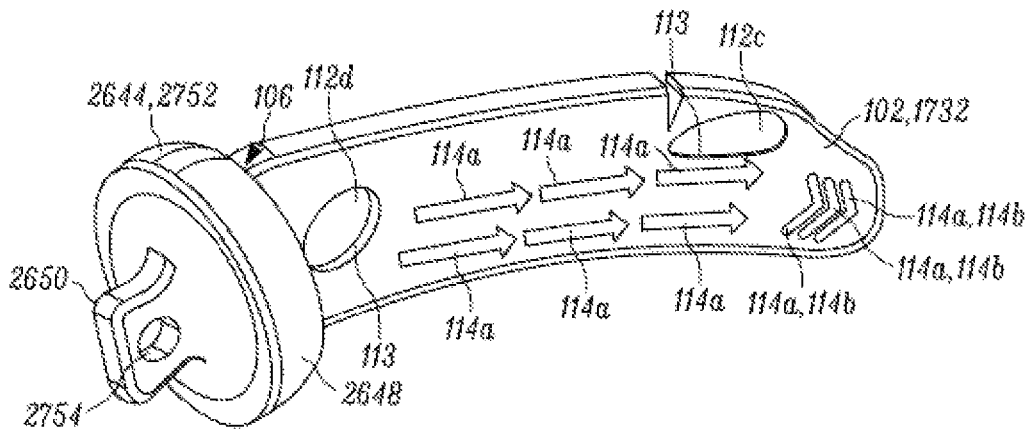

FIGS. 27-28 depict an example alternate configuration for the handle 2644, referred to as a handle B 2752. The handle B 2752 is substantially similar to the handle A 2646, except that the handle B 2752 includes an aperture 2754 extending therethrough. The aperture 2754 may be sized to receive at least one of a string or a user's finger so that the device 100 may be maneuvered through at least one of the string and the user's finger. FIG. 27 depicts the absorbent member K 2342 connected to the handle B 2752. FIG. 28 depicts the absorbent member G 1732 connected to the handle B 2752.

Figure 29:
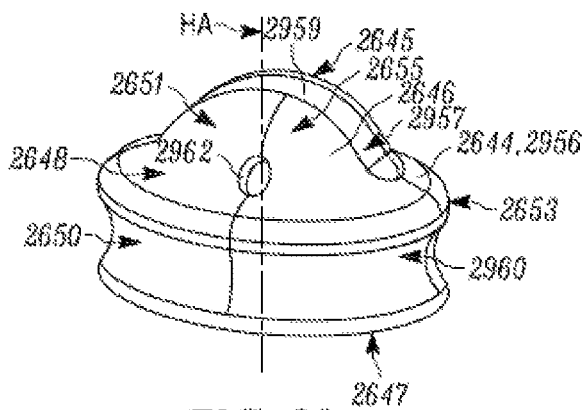
FIG. 29 is a perspective front side view of an element of the aspect of FIG. 26, in a third configuration.

FIGS. 29-36 depict an example alternate configuration for the handle 2644, referred to as a handle C 2956. The handle C 2956 has the receiving portion 2648 for receiving the absorbent member 102 and a gripping portion 2650 for maneuvering the medical packing device 100. The receiving portion 2648 of the handle C 2956 has a receiving hollow 2957 that extends from a receiving opening 2959 in the distal portion surface 2655 into the proximal portion 2653. As shown in FIG. 29, the receiving opening 2959 of the handle C 2956 may be arcuate.

Figure 30:
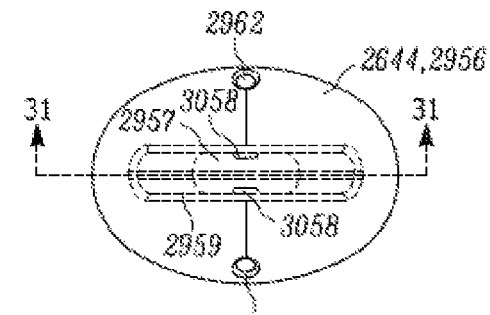
FIG. 30 is a top view of the element of the aspect of FIG. 29.
Figure 31:
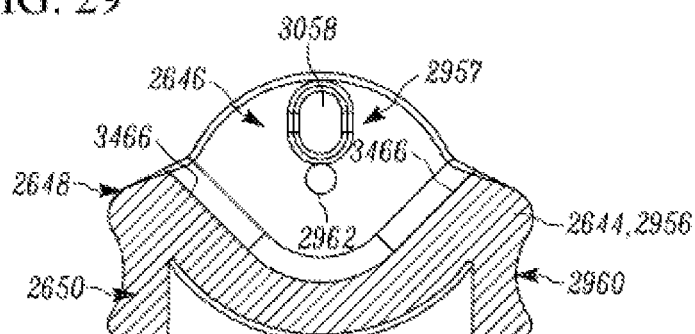
FIG. 31 is a cross-sectional view taken along line 31-31 in FIG. 30.
Figure 32:
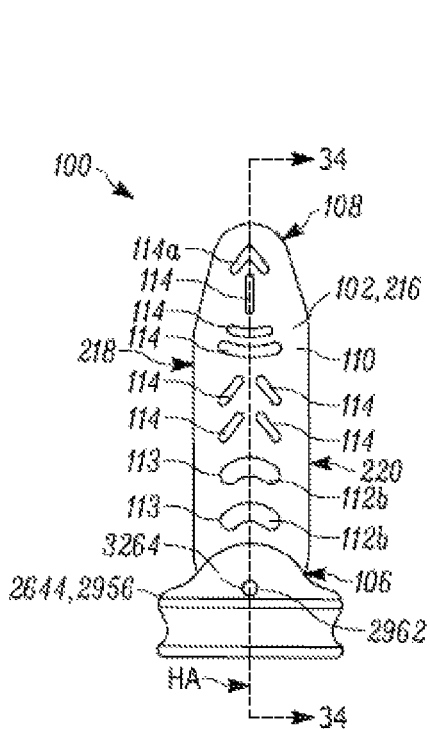
FIG. 32 is a front side view of the aspect of FIG. 26 in an example use configuration, and an the element in a third configuration.
Figure 33:
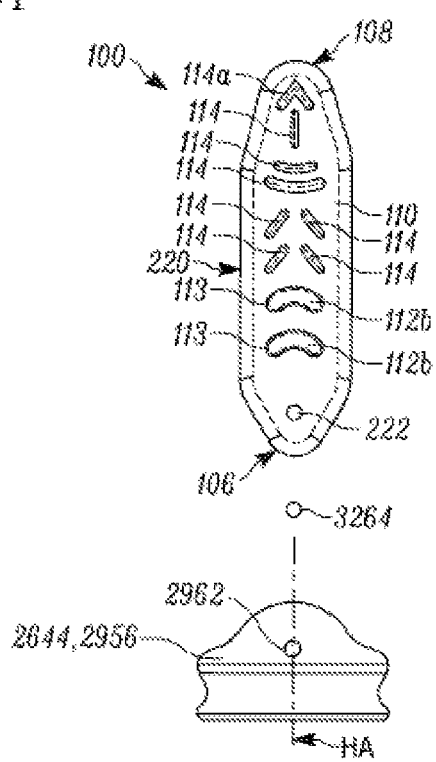
FIG. 33 is an exploded front side view of the aspect of FIG. 32.

As shown in FIGS. 30-31, the receiving hollow 2957 of the receiving portion 2648 of the handle C 2956 may include at least one absorbent member support element 3058 that engages at least one of the first major side surface 110 of an absorbent member 102 and the second major side surface 218, when provided, of an absorbent member 102 that is received in the receiving portion 2648 of the handle C 2956. In other words, the at least one absorbent member support element 3058 engages at least one of the first major side surface 110 of an absorbent member 102 and the second major side surface 218, when provided, when the proximal end 106 of the absorbent member 102 is connected to the handle C 2956 and seated within the receiving hollow 2957. The engagement of the at least one absorbent member support element 3058 with at least one of the first and second major side surfaces 110, 218 of the absorbent member 102 at least partially supports the absorbent member 102 by at least partially preventing the absorbent member 102 from undesirably moving and/or pivoting in the transverse direction. As shown in FIGS. 29-36, the gripping portion 2650 of the handle C 2956 includes at least one circumferentially extending indent 2960 for use as a finger grip. In particular, the handle C 2956 is shown in FIGS. 29-36 as having one circumferentially extending indent 2960.

The handle C 2956 is configured to allow the absorbent member 102 to pivot at an angle relative to the central axis HA of the handle C 2956 so that the medical packing device 100 may be adaptable to patients having cavities, such as nasal cavities, with differing angles. In particular, the receiving portion 2648 of the handle C 2956 includes the pinhole 2962 transversally extending therethrough. As shown in FIGS. 32-36, when the handle C 2956 and an absorbent member 102, such as the absorbent member B 216, are joined together, the handle C 2956 is aligned with the absorbent member B 216 such that the pinhole 2962 is aligned with the aperture 222. A pin 3264 may extend through each of the pinhole 2962 and the aperture 220 to attach and secure the absorbent member B 216 to the handle C 2956. The absorbent member B 216 is pivotable with respect to the handle C 2956 about the pin 3264, and accordingly, at an angle relative to the central axis HA of the handle C 2956. The absorbent member B 216 may be pivotable with respect to the handle C 2956 between about ±1 and about ±90 degrees, and preferably between about ±30 and about ±60 degrees. In other words, the absorbent member B 216 may be pivotable in a clockwise C1 direction between about 1 and about 90 degrees from the central axis HA of the handle C 2956 and pivotable in a counterclockwise C2 direction between about 1 and about 90 degrees from the central axis HA of the handle C 2956.

Figure 34:
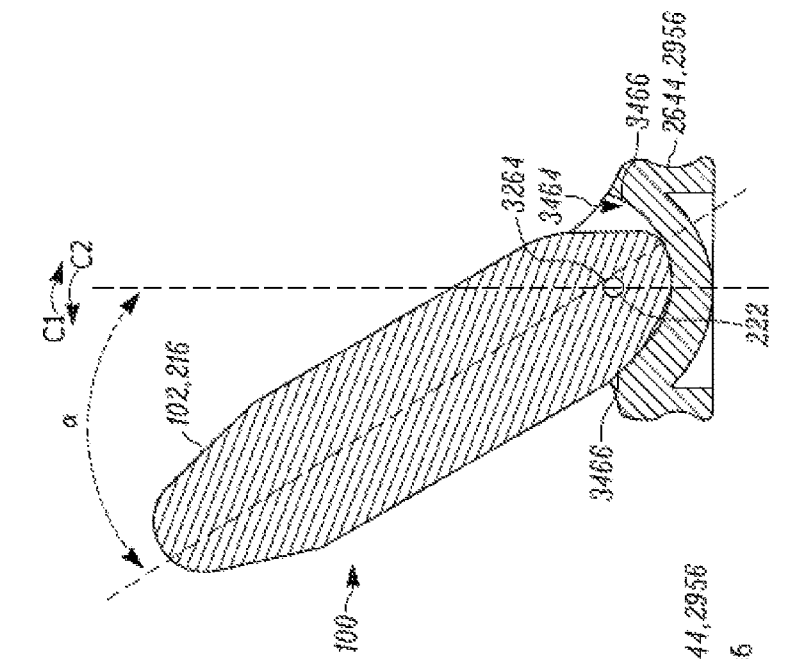
FIG. 34 is a cross-sectional view taken along line 34-34 in FIG. 32.
Figure 35:
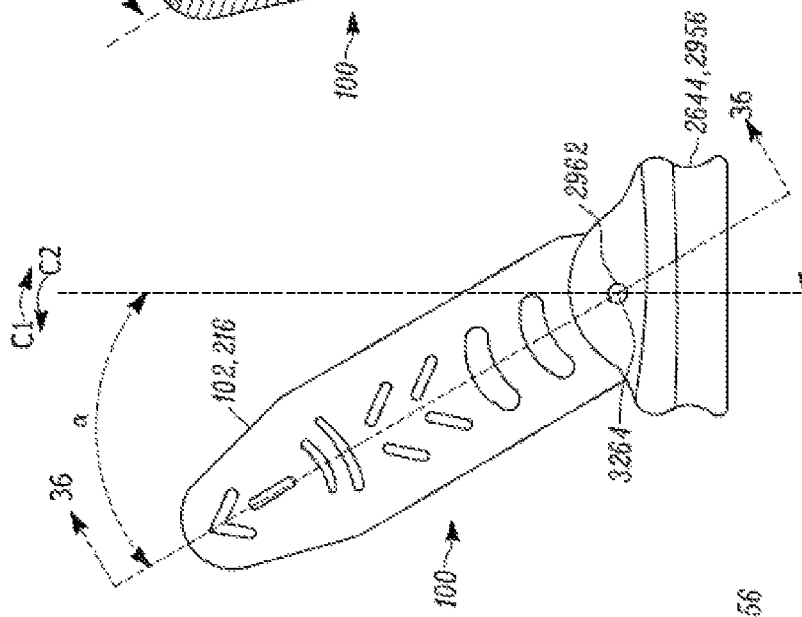
FIG. 35 is a front side view of the aspect of FIG. 32, in an example use configuration.
Figure 36:
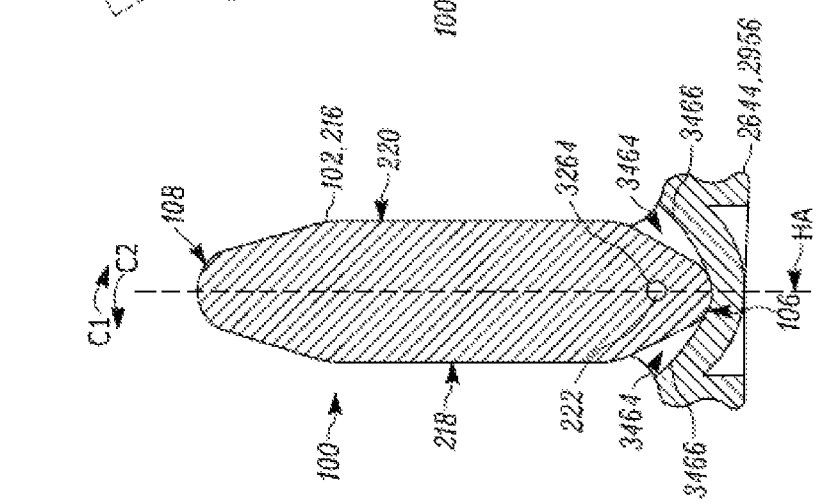
FIG. 36 is a cross-sectional view taken along line 36-36 in FIG. 35.
Figure 37:
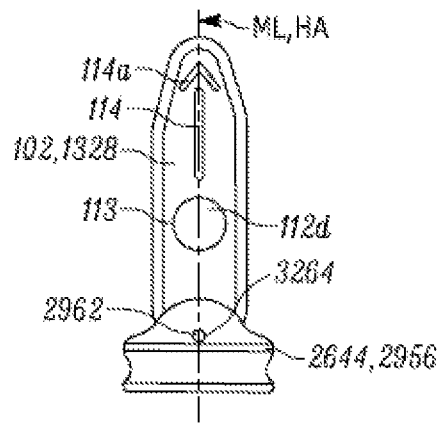
FIG. 37 is a front side view of the aspect of FIG. 26 in an example use configuration, and with an element in the third configuration.

As shown in FIGS. 34 and 36, lateral gaps 3464 between the handle 2644 and the absorbent member 102, and stop surfaces 3466 in the handle C 2956 may allow the absorbent member B 216 to pivot clockwise C1, and/or counterclockwise C2, a predetermined degreed distance a relative to the central axis HA of the handle C 2956. For example, depending on the configuration of at least one of the absorbent member B 216, the handle C 2956, the lateral gaps 3464, and the stop surfaces 3466, the absorbent member 102 may be able to pivot clockwise C1, and/or counterclockwise C2, 30 degrees from the central axis HA of the handle C 2956 until a portion of the edge 220 of the absorbent member B 216 contacts the stop surface 3466, upon which the absorbent member B 216 is prevented from pivoting any further in that direction. The configuration of at least one of the absorbent member B 216, the handle C 2956, the lateral gaps 3464, and the stop surfaces 3466 can vary in order to make the device 100 adaptable to subjects having nasal cavities with differing angles. For example, the device 100 can be manufactured to be able to pivot a full range from extreme clockwise to extreme counterclockwise at least 1, 2, 4, 5, 10, 15, 20, 30, 45 or 60 degrees and optionally not more than 180, 170, 160, 150, 140, 130, 120, 110, 100, 90, 80, 70, 60, 50, 40, 30, 20, 10, 5 or 2 degrees. FIG. 37 depicts the handle C 2956 connected to the absorbent member E 1328.

Figure 38:
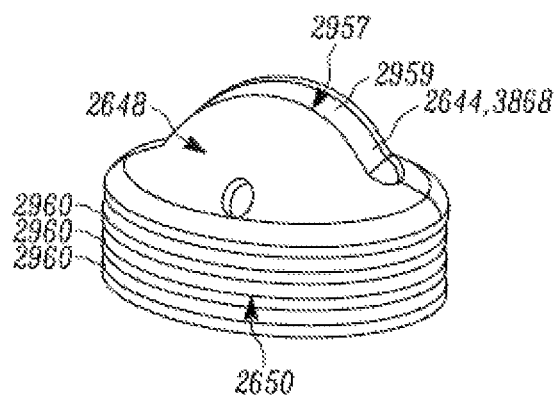
FIGS. 38-42 are perspective front side views of an element of the aspect of FIG. 26, in fourth-eighth configurations.

FIG. 38 depicts an example alternate configuration for the handle 2644, referred to as a handle D 3868. The handle D 3868 is substantially similar to the handle C 2956, except that the handle D 3868 has a plurality of circumferentially extending indents 2960 instead of having only one circumferentially extending indent 2960. In particular, the gripping portion 2650 of the handle D 3868 is shown in FIG. 38 as having three circumferentially extending indents 2960.

Figure 39:
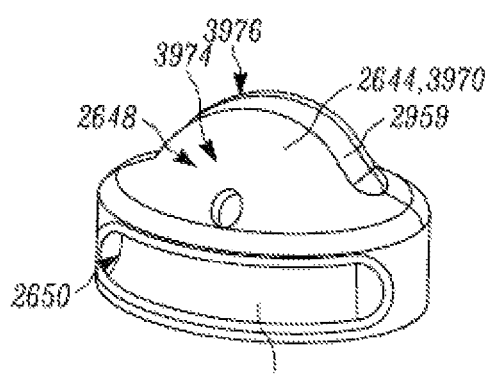

FIG. 39 depicts an example alternate configuration for the handle 2644, referred to as a handle E 3970. The handle E 3970 is substantially similar to the handle C 2956, except that the gripping portion 2650 of the handle E 3970 has at least one indent 3972 on at least one of a first major side surface 3974 and a second major side surface 3976 of the handle E 3970 instead of the at least one circumferentially extending indent 2960 of handle C 2956. In particular, the handle E 3970 is shown in FIG. 41 as having one indent 3972 on at least the first major side surface 3974.

Figure 40:
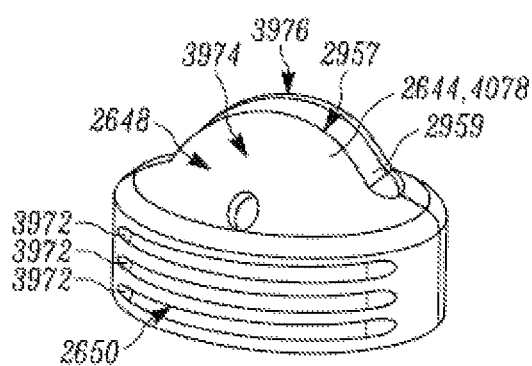

FIG. 40 depicts an example alternate configuration for the handle 2644, referred to as a handle F 4078. The handle F 4078 is substantially similar to the handle E 3970, except that the handle F 4078 has a plurality of indents 3972 on at least one of the first and second major side surfaces 3974, 3976 of the handle F 4078 instead of having only one indent 3972 on at least one of the first and second major side surfaces 3974, 3976 of the handle E 3970. In particular, the gripping portion 2650 of the handle F 4078 is shown in FIG. 40 as having three indents 3972 on at least the first major side surface 3974.

Figure 41:
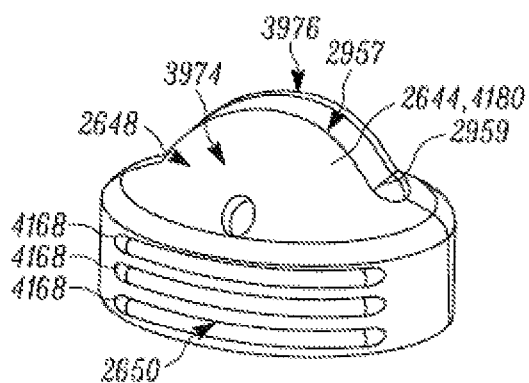

FIG. 41 depicts an example alternate configuration for the handle 2644, referred to as a handle G 4180. The handle G 4180 is substantially similar to the handle C 2956, except that the handle G 4180 has a at least one transversely extending projection 4182 on at least one of the first and second major side surfaces 3974, 3976 instead of having only one circumferentially extending indent 3760. In particular, the gripping portion 2650 of the handle G 4180 is shown in FIG. 41 as having three transversely extending projections 4182 on at least the first major side surface 3974.

Figure 42:
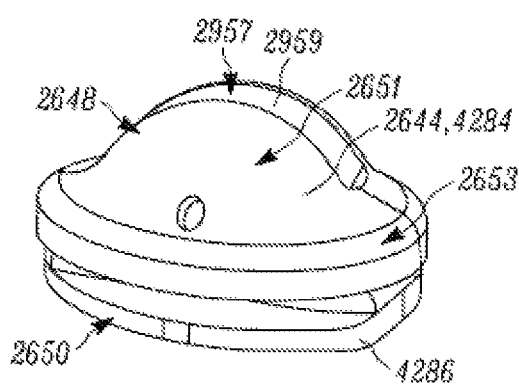
Figure 43:
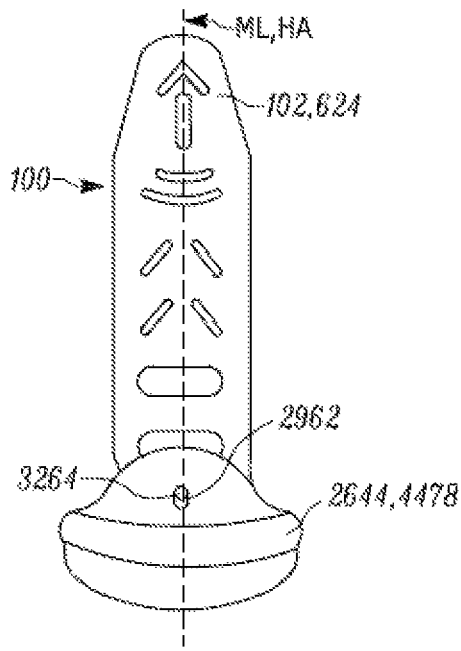
FIGS. 43-46 depict the element of the aspect of FIG. 42, in example use configurations.
Figure 44:
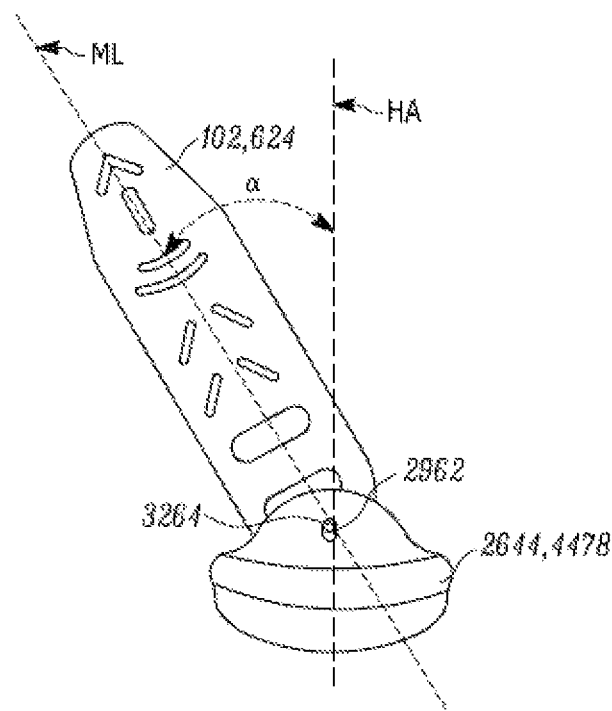
Figure 45:
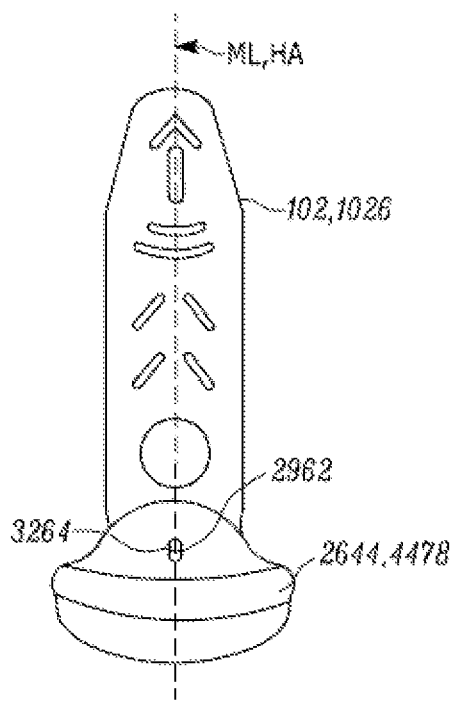
Figure 46:
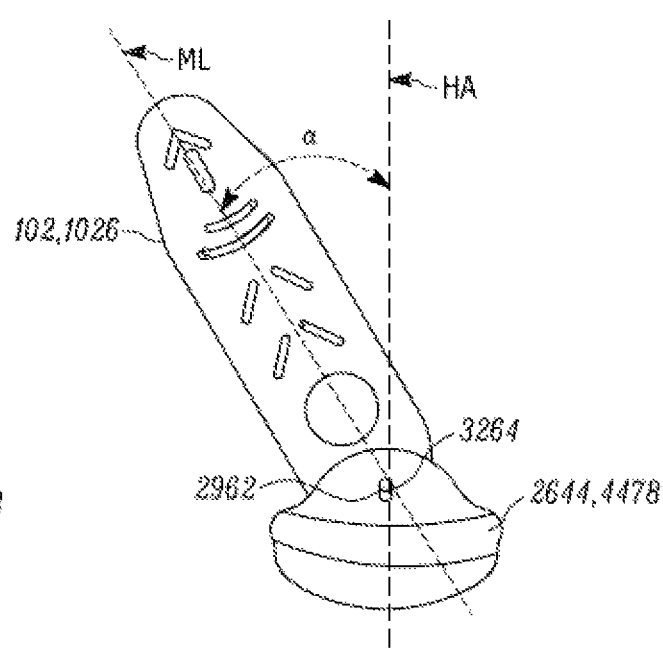

FIG. 42 depicts an example alternate configuration for the handle 2644, referred to as a handle H 4284. The handle H 4284 is substantially similar to the handle C 2956, except that the gripping portion 2650 of the handle H 4284 is a projection 4286, which can be used as a finger grip, that extends longitudinally downward from the receiving portion 2648 of the handle H 4284. FIGS. 43-44 depict the handle H 4284 connected to the absorbent member C 624. FIGS. 45-46 depict the handle H 4284 connected to the absorbent member D 1026.

Figure 47:
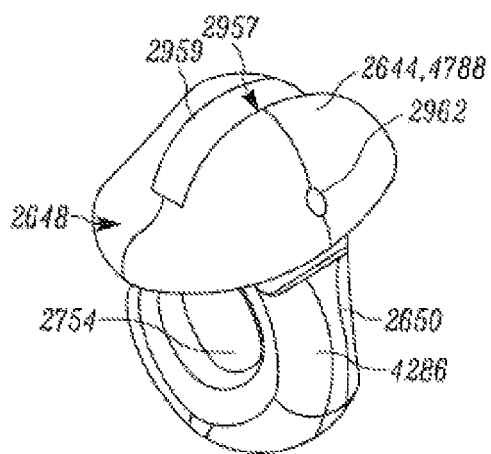
FIG. 47 is a perspective front side view of an element of the aspect of FIG. 26, in a ninth configuration.
Figure 48:
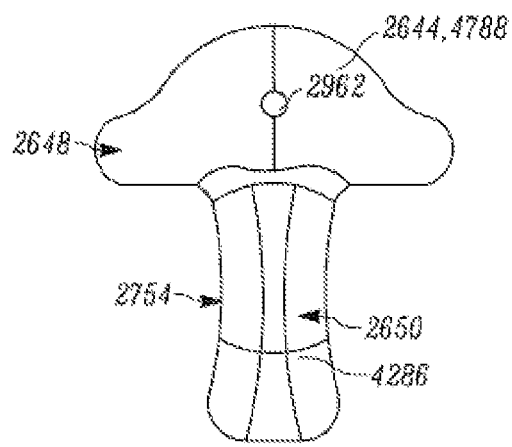
FIG. 48 is a front side view of the aspect of FIG. 47.

FIGS. 47-48 depict an example alternate configuration for the handle 2644, referred to as a handle I 4788. The handle I 4788 is substantially similar to the handle H 4284, except that the projection 4286 of the handle I 4788 includes the aperture 2754 extending therethrough. The pinhole 2962 of the receiving portion 2648 of the handle I 4788 may face a direction that is perpendicular to the direction that the aperture 2754 faces. For example, in FIGS. 47-48 the pinhole 2962 is shown facing the transverse direction while the aperture 2754 is shown facing the lateral direction.

Figure 49:
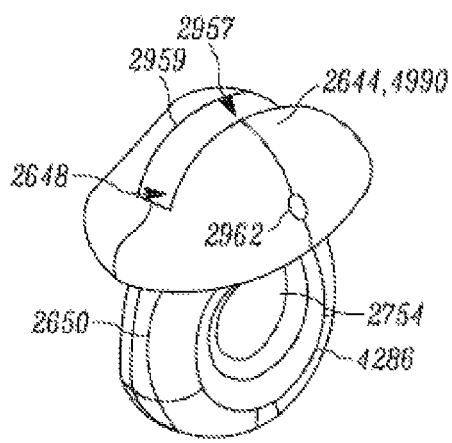
FIG. 49 is a perspective front side view of an element of the aspect of FIG. 26, in a tenth configuration.
Figure 50:
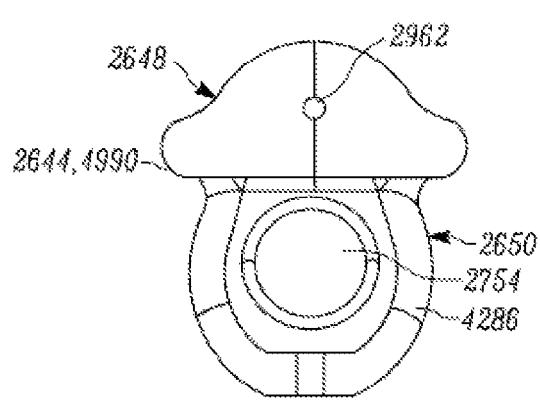
FIG. 50 is a front side view of the aspect of FIG. 49.

FIGS. 49-50 depict an example alternate configuration for the handle 2644, referred to as a handle J 4990. The handle J 4990 is substantially similar to the handle I 4788, except that the pinhole 2962 of the receiving portion 2648 of the handle J 4990 may face the same direction as the aperture 2754. For example, in FIGS. 49-50 both the pinhole 2962 and the aperture 2754 are shown facing the transverse direction.

Figure 51:
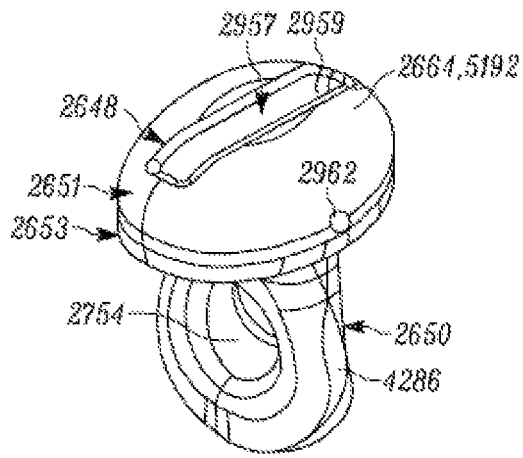
FIG. 51 is a perspective front side view of an element of the aspect of FIG. 26, in an eleventh configuration.
Figure 52:
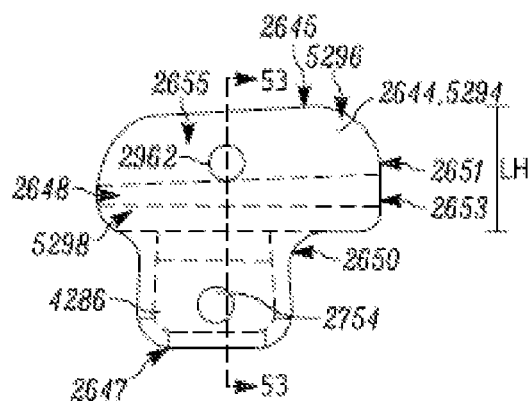
FIG. 52 is a front side view of an element of the aspect of FIG. 26, in a twelfth configuration.
Figure 53:
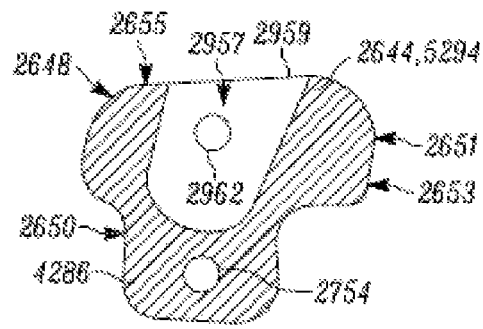
FIG. 53 is a cross-sectional view taken along line 53-53 in FIG. 52.
Figure 54:
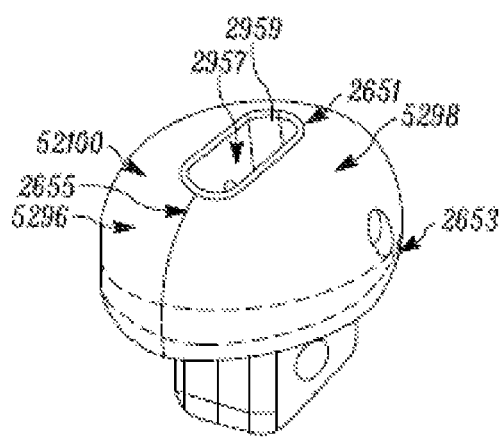
FIG. 54 is a perspective front side view of the aspect of FIG. 52.
Figure 55:
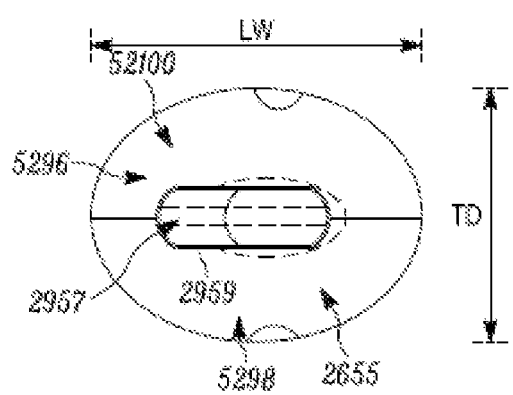
FIG. 55 is a top view of the aspect of FIG. 52.

FIG. 51 depicts an example alternate configuration for the handle 2644, referred to as a handle K 5192. The handle K 5192 is substantially similar to the handle I 4788, except that the receiving portion 2648 of the handle K 5192 is substantially egg-shaped.

FIGS. 52-55 depict an example alternate configuration for the handle 2644, referred to as a handle L 5294. The distal portion 2651 of the receiving portion 2648 of the handle L 5294 has the distal portion surface 2655 with a convex-shaped portion 5296. The convex-shaped portion 5296 has a smooth rounded shape. The receiving portion 2648 of the handle L 5294 has a lateral width LW, a transverse depth TD, and a longitudinal height LH. The lateral width LW is greater than the transverse depth TD so that the receiving portion 2648 has an oblong shape, as shown in FIG. 30. The oblong shape may be an oval. The receiving portion 2648 of the handle L 5294 has a receiving hollow 2957 that extends from a receiving opening 2959 in the distal portion surface 2655 into the proximal portion 2653.

Figure 56:
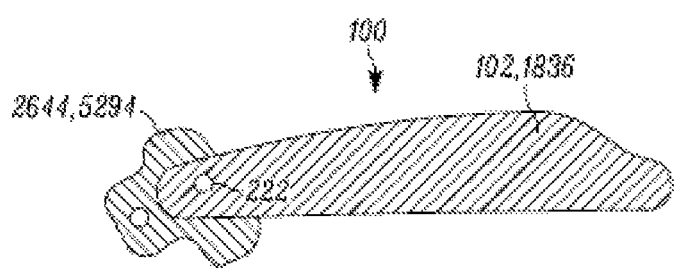
FIG. 56 is a cross-sectional view of the aspect of FIG. 52, in an example use configuration.

The handle L 5294 may have the gripping portion 2650 that is the projection 4286, which can be used as a finger grip, that extends longitudinally downward from the receiving portion 2648 of the handle H 4284. Alternatively, the handle L 5294 may not include the projection 4286. In such case, first and second major side surfaces 5298, 52100 of the receiving portion 2648 may be used by the user to grip the receiving portion 2648 of the handle L 5294 to maneuver the medical packing device 100, and thus the receiving portion 2648 may also act as the gripping portion 2650. FIG. 56 depicts the handle L 5294 connected to the absorbent member H 1836.

Those of skill in the art will understand that any of the above alternate configurations of the absorbent member 102 may be connected to and utilized with any of the alternate configurations of the handle 2644.

The medical packing device 100 may be utilized to treat epistaxis in a subject. The medical packing device 100 may be provided to a user in conventional packaging (not shown), removed from the packaging, and then inserted into a nasal cavity of the subject for a sufficient time to absorb any blood and/or bodily fluids.

Additionally, prior to inserting the medical packing device 100 intranasally, a user may mix bismuth subgallate, or another hemostatic compound, with oxymetazoline, or any other vasoconstriction agent, in the proportions described in U.S. Pat. No. 9,248,186, the entire contents of which are incorporated herein by reference. The resulting fluid or paste may be applied to the absorbent member 102 of the medical packing device 100, such as by dipping or brushing. Because the at least one depression 112, when provided, forms a reservoir capable of receiving and retaining a volume of medicament, the at least one depression 112 receives and retains a predetermined amount of the mixture of bismuth subgallate, or another hemostatic compound, with oxymetazoline, or any other vasoconstriction agent. The absorbent member 102 may then be inserted intranasally. With the absorbent member 102 inserted, the bismuth subgallate and the oxymetazoline collectively work to treat the epistaxis.

Instead of applying the mixture of bismuth subgallate, or another hemostatic compound, with oxymetazoline, or any other vasoconstriction agent, at the time of use, the absorbent member 102 of the medical packing device 100 may be coated or impregnated with a mixture of a hemostatic compound and a liquid pharmaceutical excipient during the manufacture of the medical packing device 100, as will be discussed below. In such case, when the epistaxis is noticed, the absorbent member 102 may be inserted intranasally. Further, if a user desires, a liquid vasoconstriction agent may be applied to the coated absorbent member 102 prior to the insertion of the absorbent member 102. With the absorbent member 102 inserted, the hemostatic compound and the vasoconstriction agent collectively work to treat the epistaxis.

Instead of, or in addition to treating epistaxis, the medical packing device 100 may be utilized to deliver a medicament to a subject. In such case, the medicament delivery device 100 is provided to a user. At least one medicament may be applied to the absorbent member 102. The medicament may be selected from a group consisting of a hemostatic compound, a vasoconstriction agent, a liquid pharmaceutical excipient, a drug, a pharmaceutical compound, and a combination thereof. Because the at least one depression 112, when provided, forms a reservoir capable of receiving and retaining a volume of medicament, the at least one depression 112 receives and retains a predetermined amount of the medicament. With the at least one medicament applied to the absorbent member 102, at least a portion of the absorbent member 102 is inserted into a nasal cavity of the subject for a time sufficient to allow delivery of the medicament from the at least one depression 112, when provided, to anatomical tissue adjacent to the at least one depression 112 in the cavity, such as, but not limited to, a nasal mucosa of the subject. For example, a drug or pharmaceutical compound may be applied or coated on the absorbent member 102, and in particular, provided in the at least one depression 112. The drug or pharmaceutical compound can be selected from a group consisting of: antibiotics, opioids, anti-inflammatory agents, analgesics, any other appropriate drug, any other appropriate drug or pharmaceutical compound, and any mixtures thereof. The absorbent member 102 may then be inserted intranasally into a subject to administer the drug or pharmaceutical compound intranasally.

Further, as another example, the drug or pharmaceutical compound can be mixed with a liquid pharmaceutical excipient (preferably glycerin), as described above, preferably in the ratios and with the viscosities mentioned herein. The mixture may then be coated on the absorbent member 102 in any of the manners as described above. The coated absorbent member 102 may then be inserted intranasally into a subject. The drug or pharmaceutical compound will then be absorbed or otherwise taken up by the subject.

Instead of applying and/or coating the absorbent member 102 with a drug or pharmaceutical compound in order to administer the drug or pharmaceutical compound intranasally, the drug or pharmaceutical compound can be in the form of a bead or a powder, which can be embedded or impregnated in the absorbent member 102 or in pores of the absorbent member 102. Once the absorbent member 102 is inserted intranasally, the drug or pharmaceutical compound will then be absorbed or otherwise taken up by the subject.

The above descriptions of delivery a drug or pharmaceutical compound to a subject intranasally allows the user to expedite systematic delivery of the drug or pharmaceutical compound when venous access is not desirable and/or possible given certain situations.

Those having skill in the art will understand that any medicament known in the art may be used and/or delivered to any cavity of a subject using any of the above sequences of use, or any portions of the above sequences of use, with any of the absorbent member 102 and/or handle 2644 configurations.

In order to manufacture the medical packing device 100, an absorbent member 102 comprising the oppositely disposed first and second major side surfaces 110, 218 is provided. The absorbent member 102 may be at least partially formed of a dried and compressed absorbent sponge or foam as known in the nasal packing art; preferably made of synthetic flexible or soft foam such as polyvinyl acetate (PVAc) foam or polyvinyl alcohol (PVA) foam or urethane foam, preferably open cell foam, preferably Ivalon brand polyvinyl acetal sponge or foam from Carwild or FABCO; Gelfoam brand PVA foam; PVA sponge from Merocel, PVA foam from Genadyne; Rhino Rocket nasal packing from Shippert Medical; or Hydrasorb brand urethane foam. Less preferably the absorbent member 102 can be made of polyethylene oxide, partially hydrolyzed polyvinyl acetate, hydroxylethyl cellulose, hydroxylpropyl cellulose, methyl cellulose, and modified starch, preferably in the form of compressed flexible foam or sponge.

The at least one depression 112 may be formed on at least one of the first and second major side surfaces 110, 218 of the absorbent member 102. The at least one depression 112 forms a reservoir capable of receiving and retaining a volume of a medicament. The at least one impressed marking 114 may be formed on at least one of the first and second major side surfaces 110, 218 of the absorbent member 102. The at least one depression 112 and/or the at least one impressed marking 114 may be formed by at least one of a debossing process, an impressing process, an etching process, a stamping process, a carving process, or by any other suitable process. The aperture 222 that extends transversely between the first and second major side surfaces of the absorbent member 102 may be formed and positioned at the proximal end of the absorbent member 102. For example, the aperture 222 may be formed by a hole transversely through the absorbent member 102.

All or only portion of the absorbent member 102 may be coated with a medicament. The medicament used to coat the absorbent member 102 may be selected from a group consisting of a hemostatic compound, a vasoconstriction agent, a liquid pharmaceutical excipient, a drug, a pharmaceutical compound, and a combination thereof. For example, the absorbent member 102 may be coated with a mixture of a hemostatic compound and a liquid pharmaceutical excipient during the manufacture of the medical packing device 100. The hemostatic compound is preferably a powder and is preferably a bismuth-containing compound. The bismuth-containing compound is preferably selected from a group consisting of bismuth subgallate, bismuth subnitrate, bismuth subcarbonate, bismuth tribromophenate and mixtures thereof. More preferably, the bismuth-containing compound is bismuth subgallate in powder form.

The liquid pharmaceutical excipient is preferably selected from a group consisting of non-polar solvents, organic solvents, water-soluble organic solvents (such as polyethylene glycol, propylene glycol, glycerin, ethanol and isopropanol), water-insolublelipids (such as almond oil, canola oil, castor oil, corn oil, cottonseed oil, mineral oil, olive oil, peanut oil, sesame oil, soybean oil, sunflower oil, and vegetable oil), petroleum jelly, and mixtures of any of the foregoing. More preferably the liquid pharmaceutical excipient is glycerin.

The hemostatic compound (preferably bismuth subgallate) and the liquid pharmaceutical excipient (preferably glycerin) are preferably mixed in the following ratio: 0.5-4, more preferably 1-3, and even more preferably about 2 grams liquid pharmaceutical excipient per 1 gram hemostatic compound. The mixture of the hemostatic compound and the liquid pharmaceutical excipient is preferably about as viscous as honey or less viscous. The absorbent member 102 is then coated with the mixture of the hemostatic compound and the liquid pharmaceutical excipient by at least one of brush coating, roll coating, dip coating, and spray coating.

Alternatively to the above, the pharmaceutical excipient may be applied to the absorbent member 102 and soaked into the absorbent member 102. Once the pharmaceutical excipient is soaked into the absorbent member 102, the absorbent member 102 may be coated with the powdered hemostatic compound. Thus, the pharmaceutical excipient may be absorbed into the absorbent member 102 while the hemostatic compound stays in exterior pores of the absorbent member 102. Any excess material that has been applied to the absorbent member 102 may be at least one of blown off, wiped off, and scraped off of the absorbent member 102.

The benefit to this above process of coating the absorbent member 102 with a mixture of a hemostatic compound and a liquid pharmaceutical excipient during the manufacture of the medical packing device 100 is that the pharmaceutical excipient, being mostly or completely non-aqueous, may not cause the absorbent member 102 to substantially expand from the collapsed condition or go limp.

If desired, the handle 2644 may be provided and connected to the proximal end 106 of the absorbent member 102. If the absorbent member 102 has the aperture 222 and the user desires the absorbent member 102 of the medical packing device 100 to pivot with respect to the handle 2644, a handle 2644 having the pinhole 2962 is provided. In such case, the pinhole 2962 of the handle 2644 is aligned with the aperture 222 of the absorbent member 102. With the pinhole 2962 and the aperture 222 aligned, the pin 3264 is inserted through each of the aligned pinhole 2962 and aperture 222 to secure the absorbent member 102 to the handle 2644 such that the absorbent member 102 is pivotable with respect to the handle 2644 about the central axis of the handle 2644 and about the pin 3264. The medical packing device 100 may then be sealed in a conventional package (not shown) and preferably put in a kit with a container of vasoconstriction agent, which is preferably oxymetazoline.

The handle 2644 and the pin 3264, when provided, can be at least partially formed from silicone, polyethylene, polypropylene, polycarbonate, polyamides, stainless steel, titanium, rubber, any other suitable material, or any combination thereof.

It is contemplated that any nasal packing as known in the art, preferably the absorbent member 102 described above, with or without the handle 2644, preferably made of the materials described above, can be embedded, impregnated and/or coated with a drug or pharmaceutical compound and preferably with the liquid pharmaceutical excipient, all as described above, and administered intranasally or administered in other anatomical locations, where preferably it will expand from the compressed condition to the expanded condition. Optionally, before or after insertion into the location or cavity, the nasal packing, preferably the absorbent member 102 of the medical packing device 100, can be wetted with an aqueous solution to initiate expansion. Alternatively, or instead, expansion can be initiated by the presence of aqueous bodily fluids.

It is contemplated that the swelling time of the absorbent member 102 can be varied. For example, the expansion rate of the absorbent member 102, preferably made of PVAc or PVA, can be controlled by varying an amount of liquid pharmaceutical excipient loading on and/or across the absorbent member 102, a porosity of the material that the absorbent member 102 is formed from, pore sizes of the material that the absorbent member 102 is formed from, the degree the absorbent member 102 is compressed during manufacture, the size and number of depressions 112 and/or impressed markings 114 on the absorbent member 102, and the arrangement of the depressions 112 and/or impressed markings 114 (e.g., by arranging the depressions 118 and/or impressed markings 116 on the first major side surface 110 of the absorbent member 102 to be either symmetrical or staggered with the depressions 112 and/or impressed markings 114 on the second major side surface of the absorbent member 102). Further, the expansion rate of the absorbent member 102 can be controlled by the amount or the ability of a pharmaceutical excipient to be displaced by fluids, such as bodily fluids.

It is contemplated that by varying a pharmaceutical excipient to active medicament(s) ratio (such as the ratio of a liquid pharmaceutical excipient to a hemostatic compound), and/or the process of introducing medicament(s) to the absorbent member 102, the amount of active medicament(s) present on the absorbent member 102 and/or throughout the medical packing device 100 can be varied.

It is contemplated that a loading variation of the at least one medicament on the absorbent member 102 allows variation in the delivery of one or more active medicaments as a function of time or area of interest(s). For example, the absorbent member 102 can be coated, such as by dipping, multiple times. A first dip of the absorbent member 102 into a first medicament may be highly concentrated so that the first medicament can penetrate deeply into the absorbent member 102. A second dip into the first or a second medicament that is more dilute and/or for less time may allow a lower contraction of that medicament on the absorbent member 102. In such case, the medical packing device 100 can be optimized to release the first medicament only after the second medicament acts on the subject. For example, the device can be optimized to release a hemostatic agent, which was applied during the first dip of the absorbent member 102, after a vasoconstriction agent, which was applied during the second dip of the absorbent member 102, acts to constrict blood vessels.

It is contemplated that the medical packing device 100 can include means for delivering medicaments in situ. For example, the absorbent member 102 of the medical packing device 100 can be provided with one or more lumens (not shown) with one end exiting from the proximal end 106 of the absorbent member 102, and at least one or more distal exit points along absorbent member 102 that may be positioned to be in contact with anatomical areas of interest. Alternatively, or in addition to the above, one or more lumens (not shown) can be created by beads (fixed or not fixed) or other inert material(s) in the absorbent member 102 that create a torturous path(s). In such case, one or more medicaments may be dispensed into proximal ends of the lumen(s) for dispersion onto (and treatment of) the anatomical tissue surrounding the absorbent member 102. The medicament can be introduced to the proximal ends of the lumen(s) in the absorbent member 102 by a syringe, a luer lock connection, or any other temporary dispensing mechanism.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

The following is claimed:

1. A medical packing device for use within a body cavity of a subject, comprising:
    an absorbent member having oppositely disposed proximal and distal ends that are spaced apart in a longitudinal direction, the absorbent member having an aperture extending in a transverse direction completely through the absorbent member at an absorbent portion of the absorbent member and at the proximal end of the absorbent member, the transverse direction being substantially perpendicular to the longitudinal direction;
    a handle having a pinhole that is aligned with the aperture; and
    a pin transversely extending through each of the pinhole and the aperture to secure the absorbent member to the handle, the absorbent member being pivotable with respect to the handle about the pin.

2. The device of claim 1, wherein the absorbent member is pivotable in a clockwise direction between about 1 and about 90 degrees from the central axis of the handle and in a counterclockwise direction between about 1 and about 90 degrees from the central axis of the handle.

3. The device of claim 1, wherein the absorbent member is free from depressions and/or impressed markings.

4. The device of claim 1, wherein the absorbent member is substantially shaped as a rectangle, a cylinder, a sphere, a cone, a triangular prism, a finger, or a blade.

5. The device of claim 1, wherein the handle has a gripping portion that includes at least one circumferentially extending indent for use as a finger grip.

6. The device of claim 1, wherein the handle has a gripping portion and oppositely disposed first and second major side surfaces, and wherein the gripping portion has at least one indent on at least one of the first and second major side surfaces of the handle for use as a finger grip.

7. The device of claim 1, wherein the handle has a receiving portion for receiving the absorbent member and a gripping portion that longitudinally extends downward from the receiving portion, the gripping portion has an aperture extending therethrough that is sized to receiving at least one of a string and a finger.

8. The device of claim 1, wherein the absorbent member has at least a first major side surface and at least one depression that is formed in the first major side surface and has a predetermined shape and volume, wherein the at least one depression is defined by a continuous perimeter wall that is formed in the first major side surface and forms a reservoir capable of receiving and retaining a volume of a medicament therein.

9. The device of claim 8, wherein at least the first major side surface has at least one impressed marking that at least partially acts as a flex locus so that the absorbent member is at least partially bendable along the at least one marking.

10. The device of claim 9, including a plurality of impressed markings located on at least the first major side surface, at least one of which points toward the distal end of the absorbent member and is longitudinally spaced apart from another impressed marking at a predetermined distance so that the longitudinally spaced markings form graduation marks on the absorbent member.

11. The device of claim 9, wherein the absorbent member has a second major side surface that is oppositely disposed from the first major side surface, the at least one depression on the first major side surface is symmetrical with a second depression on the second major side surface, and the at least one marking on the first major side surface is symmetrical with a corresponding second marking on the second major side surface of the absorbent member.

12. The device of claim 9, wherein the absorbent member has a second major side surface that is oppositely disposed from the first major side surface, the at least one depression on the first major side surface is longitudinally staggered with respect to a second depression on the second major side surface of the absorbent member, and the at least one marking on the first major side surface is longitudinally staggered with respect to a second impressed marking on the second major side surface of the absorbent member.

13. The device of claim 8, wherein the absorbent member has a second major side surface that is oppositely disposed from the first major side surface, the aperture transversely extending between the first and second major side surfaces.

14. The device of claim 8, wherein the absorbent member has a second major side surface that is oppositely disposed from the first major side surface, an edge transversely extending between the first and second major side surfaces, and a notch at least partially laterally extending inward from the edge of the absorbent member between the first and second major side surfaces, the notch at least partially longitudinally separating the oppositely disposed proximal and distal ends of the absorbent member and at least partially preventing the flow of blood between the proximal and distal ends of the absorbent member.

15. The device of claim 8, wherein lateral width of the absorbent member diminishes at the distal end of the absorbent member in a direction opposite to the proximal end of the absorbent member.

16. The device of claim 15, wherein the distal end of the absorbent member has a porpoise nose configuration.

17. The device of claim 8, wherein the medicament is selected from a group consisting of a hemostatic compound, a vasoconstriction agent, a liquid pharmaceutical excipient, a drug, a pharmaceutical compound, and a combination thereof.

18. The device of claim 8, wherein the absorbent member is at least partially formed of an absorbent sponge or foam.

19. The device of claim 8, wherein the absorbent member has a blade-shaped configuration.

20. The device of claim 1, wherein the handle has a central axis extending therethrough, the absorbent member being pivotable at an angle relative to the central axis of the handle.

21. The device of claim 20, wherein the aperture is located at the proximal end of the absorbent member and transversely extends between a first major side surface and an oppositely disposed second major side surface.

22. The device of claim 21, wherein the absorbent member is pivotable in a clockwise direction between about 1 and about 90 degrees from the central axis of the handle and in a counterclockwise direction between about 1 and about 90 degrees from the central axis of the handle.

23. The device of claim 1, wherein the absorbent member has at least a first major side surface, at least the first major side surface having at least one impressed marking that at least partially acts as a flex locus so that the absorbent member is at least partially bendable along the at least one marking.

24. The device of claim 23, including a plurality of impressed markings located on at least the first major side surface, at least one of which points toward a distal end of the absorbent member and is longitudinally spaced apart from another impressed marking at a predetermined distance so that the longitudinally spaced markings form graduation marks on the absorbent member.

25. The device of claim 1, wherein the handle has oppositely disposed proximal and distal ends, the handle having a receiving portion with a distal portion disposed towards the distal end of the handle and a proximal portion that is adjacent and proximal to the distal portion, the distal portion of the receiving portion having a distal portion surface, the receiving portion having a receiving hollow that extends from a receiving opening in the distal portion surface into the proximal portion, the receiving portion has a lateral width, a transverse depth, and a longitudinal height, the lateral width being greater than the depth to define an oblong shape.

26. The device of claim 25, wherein the oblong shape is an oval.

27. The device of claim 1, wherein the handle has oppositely disposed proximal and distal ends, the handle having a receiving portion with a distal portion disposed towards the distal end of the handle and a proximal portion that is adjacent and proximal to the distal portion, the distal portion of the receiving portion having a distal portion surface, at least a portion of the distal portion surface being arcuate with respect to a lateral direction, the receiving portion having a receiving hollow that extends from a receiving opening in the distal portion surface into the proximal portion, at least a portion of the receiving opening in the distal portion surface being arcuate with respect to the lateral direction, the receiving portion having first and second major side surfaces for gripping the receiving portion of the handle;

wherein the lateral direction is substantially perpendicular to the longitudinal direction; and wherein the proximal end of the absorbent member is connected to the handle and seated within the receiving hollow.

28. The device of claim 27, wherein the handle has a gripping portion that includes at least one circumferentially extending indent for use as a finger grip.

29. The device of claim 27, wherein the handle has a gripping portion and oppositely disposed first and second major side surfaces, and wherein the gripping portion has at least one indent on at least one of the first and second major side surfaces of the handle for use as a finger grip.

30. The device of claim 27, wherein the handle has a central axis extending therethrough, the absorbent member being pivotable at an angle relative to the central axis of the handle.

31. A method of delivering a medicament to a subject, comprising:

providing the medical packing device of claim 8; and inserting at least a portion of the absorbent member into a body cavity of the subject for a time sufficient to allow delivery of the medicament from the at least one depression to anatomical tissue adjacent to the at least one depression in the body cavity.

32. The method of claim 31, further comprising:

applying the medicament to the absorbent member, the medicament being selected from a group consisting of a hemostatic compound, a vasoconstriction agent, a liquid pharmaceutical excipient, a drug, a pharmaceutical compound, and a combination thereof.

33. The method of claim 31, wherein the absorbent member is inserted into a nasal cavity of the subject for a time sufficient to allow delivery of the medicament from the at least one depression to a nasal mucosa of the subject.

* * * * *